United States Patent [19]

Grasshoff et al.

[11] Patent Number: 5,534,388
[45] Date of Patent: *Jul. 9, 1996

[54] PROCESS FOR GENERATION OF ACID AND FOR IMAGING, AND IMAGING MEDIUM FOR USE THEREIN

[75] Inventors: Jurgen M. Grasshoff, Hudson; John L. Marshall, Somerville; Richard A. Minns, Arlington; Mark R. Mischke, Arlington; Anthony J. Puttick, Arlington; Lloyd D. Taylor, Lexington; Stephen J. Telfer, Arlington, all of Mass.

[73] Assignee: Polaroid Corporation, Cambridge, Mass.

[*] Notice: The term of this patent shall not extend beyond the expiration date of Pat. No. 5,445,917.

[21] Appl. No.: 407,576

[22] Filed: Mar. 20, 1995

Related U.S. Application Data

[62] Division of Ser. No. 319,925, Oct. 7, 1994, Pat. No. 5,445,917, which is a division of Ser. No. 141,860, Oct. 22, 1993, Pat. No. 5,395,736, which is a continuation-in-part of Ser. No. 965,162, Oct. 23, 1992, Pat. No. 5,334,489.

[51] Int. Cl.$^6$ .............. G03C 1/725; G03C 1/73; G03C 1/735; G03C 5/00
[52] U.S. Cl. .............. 430/338; 430/269; 430/270.1; 430/333; 430/335; 430/336; 430/340; 430/348; 430/203
[58] Field of Search .............. 430/269, 270, 430/333, 335, 336, 338, 340, 348, 203

[56] References Cited

U.S. PATENT DOCUMENTS

| | | | |
|---|---|---|---|
| 5,102,771 | 4/1992 | Vogel et al. | 430/270 |
| 5,278,031 | 1/1994 | Boggs et al. | 430/348 |
| 5,286,612 | 2/1994 | Telfer | 430/335 |
| 5,334,489 | 8/1994 | Grasshoff et al. | 430/335 |
| 5,395,736 | 3/1995 | Grasshoff et al. | 430/270 |
| 5,401,619 | 3/1995 | Boggs et al. | 430/343 |

FOREIGN PATENT DOCUMENTS 824630  10/1969  Canada.

*Primary Examiner*—Geraldine Letscher
*Attorney, Agent, or Firm*—David J. Cole

[57] ABSTRACT

Acid can be generated by exposing a superacid precursor to actinic radiation effective to generate superacid from the superacid precursor and heating the superacid in admixture with a secondary acid generator capable of undergoing thermal decomposition to produce a secondary acid. The superacid catalyzes decomposition of the secondary acid generator, thus increasing the quantity of strong acid present in the medium. The resultant secondary acid can be used to effect a color change in an acid-sensitive material, so providing an imaging process.

8 Claims, 2 Drawing Sheets

PROCESS FOR GENERATION OF ACID AND FOR IMAGING, AND IMAGING MEDIUM FOR USE THEREIN

REFERENCE TO PARENT APPLICATION

This application is a divisional of application Ser. No. 08/319,925, filed Oct. 7, 1994 (now U.S. Pat. No. 5,445, 917), which is a divisional of Application Ser. No. 08/141, 860, filed Oct. 22, 1993 (now U.S. Pat. No. 5,395,736), which in turn is a continuation-in-part of our application Ser. No. 07/965,162, filed Oct. 23, 1992 (now U.S. Pat. No. 5,334,489).

REFERENCE TO RELATED APPLICATIONS

Attention is directed to copending application Ser. No. 07/965,172 (now U.S. Pat. No. 5,278,031), and its divisional application Ser. No. 08/106,353, filed Aug. 13, 1993 (to issue as U.S. Pat. No. 5,401,619 on Mar. 28, 1995); these two applications describe and claim a process and imaging medium generally similar to those of the present invention, but in which the breakdown of a squaric acid derivative is initiated thermally.

Attention is also directed to copending application Ser. No. 07/965,161 (now U.S. Pat. No. 5,286,612) and its continuation-in-part application Ser. No. 08/141,852 (now U.S. Pat. No. 5,453,345) of even date herewith and assigned to the same assignee as the present application; these two applications describe and claim a process and imaging medium generally similar to those of the present invention but in which acid is generated using a mixture of an infra-red dye, a superacid precursor and an acid-sensitive acid generator. This mixture is exposed to an imagewise exposure to infra-red radiation, followed by a blanket exposure to ultra-violet radiation.

Finally, attention is directed to copending application Ser. No. 08/084,759, filed Sep. 17, 1993 (to issue as U.S. Pat. No. 5,401,607 on Mar. 28, 1995) and assigned to the same assignee as the present application; this application describes and claims a process and imaging medium using a mixture of a diaryl iodonium salt and a squarylium dye capable of absorbing infra-red radiation having a wavelength within the range of about 700 to about 1200 nm, the dye having a squarylium ring the 1- and 3-positions of which are each connected, via a single $sp^2$ carbon atom, to a pyrylium, thiopyrylium, benzpyrylium or benzthiopyrylium moiety, at least one of the $sp^2$ carbon atoms having a hydrogen atom attached thereto, and the 2-position of the squarylium ring bearing an $O^-$, amino or substituted amino, or sulfonamido group. The mixture is irradiated with infra-red radiation having a wavelength within the range of about 700 to about 1200 nm, thereby causing absorption of the radiation by the squarylium dye and formation of acid in the mixture.

BACKGROUND OF THE INVENTION

This invention relates to a process for generation of acid and for imaging, and to an imaging medium for use in this imaging process.

Some conventional non-silver halide photosensitive compositions, for example photoresists, contain molecules which are inherently photosensitive, so that absorption of a single quantum brings about decomposition of only the single molecule which absorbs the quantum. However, a dramatic increase in the sensitivity of such photosensitive compositions can be achieved if the photosensitive molecule initiates a secondary reaction which is not radiation-dependent and which effects conversion of a plurality of molecules for each quantum absorbed. For example, photoresist systems are known in which the primary photochemical reaction produces an acid, and this acid is employed to eliminate acid-labile groups in a secondary, radiation-independent reaction. See, for example, U.S. Pat. Nos. 3,932,514 and 3,915,706; Reichmanis et al., Chemical Amplification Mechanism for Microlithography, Chem. Mater., 3(3), 394 (1991) and Berry et al., Chemically Amplified Resists for I-line and G-line Applications, SPIE, 1262, 575 (1990). Also, U.S. Pat. No. 5,084,371 describes a radiation-sensitive mixture which contains a water-insoluble binder which comprises a mixture of phenolic and novolak polymers and which is soluble or dispersible in aqueous alkali, and an organic compound whose solubility in alkaline developer is increased by acid, and which also contains at least one acid-cleavable group, and in addition a further group which produces a strong acid upon exposure to radiation.

U.S. Pat. No. 4,916,046 describes a positive radiation-sensitive mixture using a monomeric silylenol ether, and a recording medium produced therefrom. This patent also contains an extensive discussion of radiation-sensitive compositions which form or eliminate an acid on irradiation. According to this patent, such radiation-sensitive compositions include diazonium, phosphonium, sulfonium and iodonium salts, generally employed in the form of their organic solvent-soluble salts, usually as deposition products with complex acids such as tetrafluoroboric acid, hexafluorophosphoric acid, hexafluoroantimonic acid and hexafluoroarsenic acid; halogen compounds, in particular triazine derivatives; oxazoles, oxadiazoles, thiazoles or 2-pyrones which contain trichloromethyl or tribromomethyl groups; aromatic compounds which contain ring-bound halogen, preferably bromine; a combination of a thiazole with 2-benzoylmethylenenaphthol; a mixture of a trihalomethyl compound with N-phenylacridone; α-halocarboxamides; and tribromomethyl phenyl sulfones.

In a reaction of the type in which a primary photochemical reaction produces and acid and this acid is employed to eliminate acid-labile groups in a secondary, radiation-independent reaction, if the elimination of the acid-labile groups results in the production of a second acid (hereinafter called a "secondary" acid), the compound containing such acid-labile groups may hereinafter be referred to as a "secondary acid generator."

A secondary acid generator needs to fulfil several differing requirements. It is desirable that the material generate a strong acid, since generation of a weak acid, such as the carboxylic acids generated by some prior art processes, may limit the types of acid-sensitive compound which can be used. The secondary acid generator is desirably of low molecular weight in order to reduce the amount of material required to generate a specific amount of acid. Finally, the secondary acid generator must be compatible with all the other components of the imaging medium in which it is to be used, and should not pose environmental problems, such as offensive smell or severe toxicity.

The aforementioned copending application Ser. No. 07/965,172 discloses that certain squaric acid derivatives are effective thermal acid generators which, upon heating, liberate squaric acid or an acid derivative thereof; thus, these squaric acid derivatives can be used in thermochemical processes for the generation of acid, and for imaging.

It has now been found that breakdown of the squaric acid derivatives described in the aforementioned copending application Ser. No. 07/965,172, and of other secondary acid generators, can be catalyzed by acids which can protonate these derivatives, the efficiency of such protonation being dependent on the strength of the acid and thus greatest for very strong acids (superacids); the catalyzed breakdown of the secondary acid generators by superacids occurs rapidly at temperatures significantly lower than those required for uncatalyzed thermal breakdown of the secondary acid generators. Since superacid precursors are known which generate superacids on exposure to actinic (usually ultra-violet) radiation, a combination of a superacid precursor and one of the aforementioned secondary acid generators allows radiation-induced generation of relatively strong acid. Thus, this combination is useful for generation of acid and for imaging.

SUMMARY OF THE INVENTION

Accordingly, this invention provides an imaging process, which process comprises:

imagewise exposing a superacid precursor to actinic radiation effective to generate superacid from the superacid precursor;

heating the superacid while the superacid is admixed with a secondary acid generator capable of undergoing thermal decomposition to produce a secondary acid, the thermal decomposition of the secondary acid generator being catalyzed by the superacid, the heating being continued for a temperature and time sufficient to cause the superacid to produce secondary acid from the secondary acid generator; and simultaneously with or subsequent to the heating, contacting the secondary acid with an acid-sensitive material which changes color in the presence of the secondary acid.

In another aspect, this invention provides a process for generation of acid, which process comprises:

exposing a superacid precursor to actinic radiation effective to generate superacid from the superacid precursor; and heating the superacid while the superacid is admixed with an oxalic acid derivative capable of undergoing thermal decomposition to produce oxalic acid or an acidic derivative thereof, the thermal decomposition of the oxalic acid derivative being catalyzed by the superacid, the heating being continued for a temperature and time sufficient to cause the superacid to produce, from the oxalic acid derivative, oxalic acid or an acidic derivative thereof.

This invention also provides an imaging medium comprising:

a superacid precursor capable of generating a superacid upon exposure to actinic radiation; and a secondary acid generator capable of undergoing thermal decomposition to produce a secondary acid, the thermal decomposition of the secondary acid generator being catalyzed by the superacid, the secondary acid generator being selected from the group consisting of:

(a) a 3,4-disubstituted-cyclobut-3-ene-1,2-dione in which at least one of the 3- and 4-substituents consists of an oxygen atom bonded to the squaric acid ring, and an alkyl or alkylene group, a partially hydrogenated aryl or arylene group, or an aralkyl group, bonded to said oxygen atom, said 3,4-disubstituted-cyclobut-3-ene-1, 2-dione being capable of decomposing so as to cause replacement of the or each original alkoxy, alkyleneoxy, aryloxy, aryleneoxy or aralkyloxy group of the derivative with a hydroxyl group, thereby producing squaric acid or an acidic squaric acid derivative having one hydroxyl group; and (b) an oxalic acid derivative capable of thermal decomposition to form oxalic acid or an acidic derivative thereof.

Finally, this invention provides an imaging medium comprising:

a superacid precursor capable of generating a superacid upon exposure to actinic radiation;

a secondary acid generator capable of undergoing thermal decomposition to produce a secondary acid, the thermal decomposition of the secondary acid generator being catalyzed by the superacid; and an acid-sensitive material which changes color in the presence of the secondary acid liberated when the secondary acid generator is decomposed.

DETAILED DESCRIPTION OF THE INVENTION

As already mentioned, in the present processes a superacid precursor is exposed to actinic (typically ultra-violet) radiation, thereby generating a superacid from the precursor. The resultant superacid is heated while in admixture with a secondary acid generator capable of undergoing thermal decomposition to produce a secondary acid. This heating is continued for a temperature and time sufficient to cause the superacid to catalyze the breakdown of the secondary acid generator, so that the final quantity of secondary acid present is substantially larger than the quantity of superacid produced directly by the actinic radiation acting on the superacid precursor, although of course the second acid is typically a weaker acid than the superacid itself. This "chemical amplification" of the superacid by the secondary acid generator increases the number of moles of acid generated per einstein of radiation absorbed, and thus increases the contrast of the image produced by the present processes as compared with simple generation of acid by a superacid precursor.

The term "superacid" is used herein in its conventional sense, that is to say an acid with a $pK_a$ less than about 0. Any of the known superacid precursors, for example diazonium, phosphonium, sulfonium and iodonium compounds, may be used in this invention, but iodonium compounds are preferred. Especially preferred superacid precursors are diphenyliodonium salts, specifically (4-octyloxyphenyl)phenyliodonium hexafluorophosphate and hexafluoroantimonate and bis(N-dodecylphenyl)iodonium hexafluoroantimonate.

In the present invention, it is unbuffered superacid which catalyzes the thermal decomposition of the secondary acid generator. It is highly desirable that the processes of the invention be conducted under essentially anhydrous conditions; as chemists are well aware, the most powerful acidic species which can exist in the presence of more than one equivalent of water is the hydroxonium (hydronium) ion, $[H_3O]^+$. Accordingly, if the medium in which the present process is conducted contains water, at least part of the superacid produced by the present process will simply generate hydroxonium ion. However, in the absence of water, the superacid yields an acidic species much stronger than hydroxonium ion, and this acidic species effects the acid-catalyzed decomposition of the secondary acid generator. Typically, the present process is carried out with the superacid precursor and the secondary acid generator dispersed in a polymeric binder, and such binders can readily be chosen to provide an essentially anhydrous environment for the process.

One preferred group of secondary acid generators for use in the present invention are 3,4-disubstituted-cyclobut-3-ene-1,2-diones (hereinafter for convenience referred to as "squaric acid derivatives") in which at least one of the 3- and 4-substituents consists of an oxygen atom bonded to the squaric acid ring, and an alkyl or alkylene group, a partially hydrogenated aryl or arylene group, or an aralkyl group bonded to this oxygen atom, the 3,4-disubstituted-cyclobut-3-ene-1,2-dione being capable of decomposing so as to cause replacement of the or each original alkoxy, alkyleneoxy, aryloxy, aryleneoxy or aralkoxy group of the derivative with a hydroxyl group, thereby producing squaric acid or an acidic squaric acid derivative having one hydroxyl group. Squaric acid and its acidic derivatives are strong acids well suited to effecting color changes or other effects (for example, polymerization or depolymerization reactions) in acid-sensitive materials.

The exact mechanism by which squaric acid or an acidic derivative thereof is formed from a squaric acid derivative by superacid catalyzed thermal decomposition in the present processes may vary depending upon the type of squaric acid derivative employed. In some cases, for example di-t-butyl squarate, one or both groups attached via oxygen atoms to the squaric acid ring may decompose to yield an alkene or arene, thereby converting an alkoxy or aryloxy group to a hydroxyl group and forming the squaric acid or acidic derivative thereof. In other cases, for example 3-amino-4-(p-vinylbenzyloxy)cyclobut-3-ene-1,2-dione, there is no obvious mechanism for formation of a corresponding alkene or arene, and it appears that the mechanism of acid formation is migration of the vinylbenzyl carbocation or similar group to a different position within the molecule (probably to the amino group), and protonation of the remaining oxygen atom to form a hydroxyl group at the position from which the group migrates. In other cases, neither of these pathways is possible. However, in all cases the net effect is the replacement of the alkoxy, alkyleneoxy, aryloxy, aryleneoxy or aralkoxy group present in the original derivative with a hydroxyl group to form squaric acid or an acidic derivative thereof.

Those skilled in the art of organic chemistry will appreciate that the susceptibility to thermal decomposition of the squaric acid derivatives preferred for use in the present process is related to the stability of the cation which is produced from the ester grouping during the decomposition process. Although the stability of specific cations may be influenced by a variety of factors, including steric factors, which may be peculiar to a particular ester, in general it may be stated that the squaric acid esters preferred for use in the present process are:

(a) primary and secondary esters of squaric acid in which the α-carbon atom (i.e, the carbon atom bonded directly to the —O— atom of the squarate ring) bears a non-basic cation-stabilizing group. This cation-stabilizing group may be, for example, an $sp^2$ or sp hybridized carbon atom, or an oxygen atom;

(b) tertiary esters of squaric acid in which the α-carbon atom does not have an $sp^2$ or sp hybridized carbon atom directly bonded thereto; and (c) tertiary esters of squaric acid in which the α-carbon atom does have an $sp^2$ or sp hybridized carbon atom directly bonded thereto, provided that this $sp^2$ or sp hybridized carbon atom (or at least one of these $sp^2$ or sp hybridized carbon atoms, if more than one such atom is bonded directly to the α-carbon atom) is conjugated with an electron-withdrawing group.

It will be apparent to skilled organic chemists that, provided one of the aforementioned types of ester groupings is present in the squaric acid derivative to produce one hydroxyl group after thermal decomposition, the group present in place of the other hydroxyl group of squaric acid is of little consequence, provided that this other group does not interfere with the thermal decomposition. Indeed, the wide variation possible in this other group has the advantage that this group can be varied to control other properties of the derivative, for example its compatibility with other components of the imaging medium, or its solubility in solvents used to form coating solutions used in the preparation of the imaging medium.

Examples of squaric acid derivatives useful in the present processes include:

(a) those of the formula:

(I)

in which $R^1$ is an alkyl group, a partially hydrogenated aromatic group, or an aralkyl group, and $R^2$ is a hydrogen atom or an alkyl, cycloalkyl, aralkyl, aryl, amino, acylamino, alkylamino, dialkylamino, alkylthio, alkylseleno, dialkylphosphino, dialkylphosphoxy or trialkylsilyl group, subject to the proviso that either or both of the groups $R^1$ and $R^2$ may be attached to a polymer. Among the derivatives of Formula I, especially preferred groups are those in which (a) $R^1$ is an unsubstituted or phenyl substituted alkyl group containing a total of not more than about 20 carbon atoms, and $R^2$ is an alkyl group containing not more than about 20 carbon atoms, or a phenyl group (which may be substituted or unsubstituted); and (b) $R^1$ is a benzyl group and $R^2$ is an amino group.

(b) those of the formula:

(II)

in which $R^1$ and $R^3$ independently are each an alkyl group, a partially hydrogenated aryl group or an aralkyl group, subject to the proviso that either or both of the groups $R^1$ and $R^3$ may be attached to a polymer. Among the derivatives of Formula II, an especially preferred group are those in which $R^1$ and $R^3$ are each independently an unsubstituted or phenyl substituted alkyl group containing a total of not more than about 20 carbon atoms. Specific preferred compounds of Formula II are those in which $R^1$ and $R^3$ are each a tertiary butyl group, a benzyl group, an α-methylbenzyl group or a cyclohexyl group, namely di-tertiary butyl squarate, dibenzyl squarate, bis(α-methylbenzyl) squarate and dicyclohexyl squarate.

(c) those of the formula:

(III)

in which n is 0 or 1, and $R^4$ is an alkylene group or a partially hydrogenated arylene group. Among the derivatives of Formula III, an especially preferred group are those in which n is 1 and $R^4$ is an alkylene group containing not more than about 12 carbon atoms.

(d) those having at least one unit of the formula:

(IV)

in which n is 0 or 1, and $R^5$ is an alkylene or partially hydrogenated arylene group. In addition to the fragmentable groups $R^5$, the compounds may also contain one or more units in which a non-fragmentable group is attached to a squarate ring, directly or via an oxygen atom.

The squaric acid derivatives of Formula IV include not only high polymers, but also dimers, trimers, tetramers, etc. including at least one of the specified units. The terminating groups on the derivatives of Formula IV may be any of groups $OR^1$ or $R^2$ discussed above with reference to Formula I. Thus, for example, Formula IV includes the squaric acid dimer derivative of the formula:

The squaric acid derivatives of Formulae I and II are usually monomeric. However, these derivatives of Formulae I and II can be incorporated into polymers by having at least one of the groups $R^1$, $R^2$ and $R^3$ attached to a polymer. Attachment of the squaric acid derivatives to a polymer in this manner may be advantageous in that it may avoid incompatibility and/or phase separation which might occur between a monomeric squaric acid derivative of Formula I or II and a polymeric binder needed in an imaging medium.

The attachment of the groups $R^1$, $R^2$ and $R^3$ to a polymer may be effected in various ways, which will be familiar to those skilled in the art of polymer synthesis. The squaric acid derivatives may be incorporated into the backbone of a polymer, for example in a polymer similar to the dimer of the formula given above. Alternatively, the squaric acid derivatives may be present as sidechains on a polymer; for example, one of the groups $R^1$, $R^2$ and $R^3$ could contain an amino group able to react with a polymer containing a carboxyl groups or derivatives thereof to form an amide linkage which would link the squaric acid derivative as a sidechain on to the polymer, or these groups may contain unsaturated linkages which enable the squaric acid derivatives to be polymerized, either alone or in admixture with other unsaturated monomers.

In the present process, it is generally undesirable to form substantial quantities of gas during the superacid-catalyzed decomposition of the squaric acid derivative (or other secondary acid generator), since such gas may distort the medium containing the squaric acid derivative or form vesicles therein, and such distortion or vesicle formation may interfere with proper image formation. Accordingly, if the decomposition of the squaric acid derivative yields an alkene, it is desirable that the groups $R^1$, $R^3$, $R^4$ and $R^5$ be chosen so that this alkene is a liquid at 20° C., and preferably higher, since some heating of the alkene will inevitably occur during the superacid-catalyzed decomposition. In some cases, however, the alkene liberated may be sufficiently soluble in the medium containing the squaric acid derivative that liberation of a highly volatile alkene will not result in distortion of, or vesicle formation in, the medium.

Another preferred group of secondary acid generators for use in the present process are oxalic acid derivatives which undergo superacid-catalyzed breakdown to give oxalic acid or an acidic derivative thereof, for example an oxalic acid hemiester. Although oxalic acid and its acidic derivatives are not quite such strong acids as squaric acid and its acidic derivatives, oxalic acid and its derivatives are sufficiently strong acids for most purposes for which secondary acids are required in the present process. Also, oxalic acid derivatives are, in general, less costly than squaric acid derivatives.

The types of oxalic acid derivatives preferred for use in the present process are rather more diverse in structure than the squaric acid derivatives, and the choice of oxalic acid derivative for any specific process may be governed more by the thermal breakdown properties of the derivative than its exact chemical structure; in general, for practical reasons such as the limited temperature range to which other components of the imaging medium may safely be exposed, it is preferred that the oxalic acid derivative be one which begins to decompose thermally at a temperature in the range of about 140° to about 180° C., as measured by differential scanning calorimetry in a nitrogen atmosphere at a 10° C./minute temperature ramp, in the absence of any catalyst. Since the presence of a superacid catalyst lowers the thermal decomposition temperature of oxalic acid derivatives by at least about 20° C. and potentially significantly more, derivatives which decompose uncatalyzed at about 140° to about 180° C., will, in the presence of superacid, decompose at temperatures as low as about 65° C., temperatures to which other components of the imaging medium can in general be exposed.

The factors affecting the ability of the oxalic acid derivatives to undergo superacid-catalyzed thermal decomposition are similar to those affecting the ability of the aforementioned squaric acid derivatives to undergo the same reaction, and thus the preferred ester groups are of the same types. Accordingly, preferred oxalic acid derivatives for use in the present process include:

(a) primary and secondary esters of oxalic acid in which the α-carbon atom (i.e, the carbon atom bonded directly to the —O— atom of the oxalate grouping) bears a non-basic cation-stabilizing group. This cation-stabilizing group may be, for example, an $sp^2$ or sp hybridized carbon atom, or an oxygen atom;

(b) tertiary esters of oxalic acid in which the α-carbon atom does not have an $sp^2$ or sp hybridized carbon atom directly bonded thereto; and (c) tertiary esters of oxalic acid in which the α-carbon atom does have an $sp^2$ or sp hybridized carbon atom directly bonded thereto, provided that this $sp^2$ or sp hybridized carbon atom (or at least one of these $sp^2$ or sp hybridized carbon atoms, if more than one such atom is bonded directly to the α-carbon atom) is conjugated with an electron-withdrawing group.

(d) an ester formed by condensation of two moles of an alcohol with the bis(hemioxalate) of a diol, provided that the ester contains at least one ester grouping of types (a), (b) or (c) above. One example of an ester of this type is that of the structure:

which can be regarded as formed from two moles of menthol (2-methylethyl-4-methylcyclohexanol) and one mole of the bis(hemioxalate) of 1,6-bis(4-hydroxymethylphenoxy)hexane. Since the structure of the central residue of the diol in such esters can vary widely, the solubility and other properties of the esters can be "tuned" as required for compatibility with other components of the imaging medium, while the nature of the end groups, which undergo the acid-forming thermal decomposition, can be varied independently of the nature of the central residue.

(e) polymeric oxalates derived from polymerization of oxalate esters having an ethylenically unsaturated group, provided that the ester contains at least one ester grouping of types (a), (b) or (c) above. As with the squaric acid derivatives discussed above, use of a polymeric oxalate rather than a monomeric one may be advantageous in that it may avoid incompatibility and/or phase separation which might occur between a monomeric derivative and a polymeric binder needed in an imaging medium. Use of a polymeric derivative also tends to inhibit diffusion of the oxalate through the imaging medium during storage prior to imaging. Although polymeric oxalates can be formed in other ways, at present we prefer to form such oxalates by first forming an oxalate ester in which one of the ester groupings comprises an ethylenically unsaturated group, and then polymerizing this ester using a conventional free radical polymerization initiator, for example azobis(isobutyronitrile) (AIBN). The ethylenically unsaturated group is conveniently an acrylate or methacrylate group, while the other ester grouping in the monomeric oxalate can be any of the types discussed above.

(f) Condensation polymers of oxalates, provided that the ester contains at least one ester grouping of types (a), (b) or (c) above. This type of polymer also possesses the advantages discussed under (e) above.

Although the present process may be used for other purposes, such as triggering an acid-catalyzed chemical reaction (for example, polymerization or depolymerization reactions), it is primarily intended for use in image formation processes, and thus, simultaneously with or subsequent to the heating of the secondary acid generator and the superacid, the secondary acid liberated is desirably contacted with an acid-sensitive material which changes color in the presence of the secondary acid. (It will be appreciated that the "color change" involved in such an imaging process need not be a visible color change. If, for example, the present process is used to provide security markings intended to be machine-readable, the "color change" could be a change in absorption from one non-visible wavelength to another, such that it can be detected by the appropriate machine-reading device.) Also, desirably the exposure of the superacid precursor to the actinic radiation is effected in an imagewise manner so that the color change of the acid-sensitive material occurs only in areas which have been exposed to actinic radiation, thereby forming an image.

The acid-sensitive material used in the process of the present invention may be any material which undergoes a color change in the presence of acid. Thus any conventional indicator dye may be used as the acid-sensitive material, as may the leuco dyes disclosed in the aforementioned U.S. Pat. Nos. 4,602,263; 4,720,449 and 4,826,976, which are also sensitive to acid.

To prevent premature color formation in an imaging process of the present invention prior to the exposure step, and thus avoid the increase in $D_{min}$ which may occur when some prior art imaging media are stored for long periods before use, advantageously, prior to the exposure step, the acid-sensitive material is in admixture with an amount of a basic material insufficient to neutralize all the acid capable of being liberated by the superacid precursor. The provision of this basic material serves to "soak up" minor amounts of acid which may be generated by decomposition of the superacid precursor by, for example, accidental exposure of the medium to ultraviolet light during transportation and storage. Upon exposure, the large amount of acid generated by the superacid precursor and secondary acid generator overwhelms the amount of basic material, leaving excess acid which effects the color change in the acid-sensitive material.

The exposure of the superacid precursor to the actinic (typically ultraviolet) radiation can be effected in any of the ways conventionally used for exposing media to the same type of radiation. Thus, for example, the present medium can be exposed using the G-line from a mercury arc lamp. In some cases, it may be convenient to employ an ultra-violet laser. The use of a laser is a convenient way to record data as an image pattern in response to transmitted signals, such as digitized information.

Some imaging media of the present invention (for example those intended for use as photoresists and containing polymerizable monomers or oligomers or depolymerizable polymers) may comprise only a single layer containing all the components of the imaging medium. However, media containing an acid-sensitive material desirably comprise two separate layers or phases, so that, prior to the heating, the acid-sensitive material is present in a layer or phase separate from the layer or phase containing the superacid precursor and the secondary acid generator, and following the generation of the secondary acid from the secondary acid generator, the two layers or phases are mixed, thereby effecting the color or other change in the acid-sensitive material.

In principle, the mixing of the acid-sensitive material with the superacid precursor and secondary acid generator should be effected after the generation of the secondary acid from the secondary acid generator. However, in practice if the superacid precursor and secondary acid generator are present in one layer of a two-layer imaging medium, and the acid-sensitive material in the other layer of the medium, these two layers being such that their diffusible components mix on heating, both the generation of the secondary acid and the mixing of the two layers may be effected in a single heating step, since the superacid-catalyzed decomposition of the secondary acid generator will typically be essentially complete before mixing of the two layers becomes significant.

When a two-layer structure is used, it is not necessary that the two layers be affixed to one another before imaging. The production of secondary acid in exposed regions effected by the present process is a "permanent" chemical change, and hence it is possible to delay contacting the exposed medium with an acid-sensitive material for a substantial time. (Obviously, excessive delay may reduce the quality of an image produced by allowing secondary acid to diffuse from exposed into unexposed areas of the medium.) Accordingly, the two layers of the imaging medium may be laminated together after the second irradiation. However, in general it is most convenient to form the two layers by coating one on the other, or laminating the two layers together before imaging, since in this way only a single sheet of material has to handled during the imaging process. Since it is important that the two layers not mix prematurely, if the two layers are to be coated successively on to a support, it is usually desirable to coat one layer from an aqueous medium and the other from a non-aqueous medium. Typically, the layer containing the superacid precursor is coated from an organic solution and the layer containing an acid-sensitive leuco dye or other material is coated from an aqueous dispersion.

As already mentioned, prior to the heating step, the acid-sensitive material may be in admixture with an amount of a basic material insufficient to neutralize all the secondary acid liberated by the secondary acid generator during the heating, so that the secondary acid liberated by the secondary acid generator during the heating neutralizes all of the basic material and leaves excess secondary acid sufficient to effect the change in the acid-sensitive material. The provision of this basic material serves to "soak up" minor amounts of acid which may be generated in unexposed areas after exposure due, for example, to slow decomposition of the superacid precursor during protracted storage. Since obviously the basic material cannot be allowed to contact the superacid prior to the heating step, desirably the acid-sensitive material is present in a layer or phase separate from the layer or phase containing the superacid precursor and the secondary acid generator and, following the generation of the secondary acid, the two layers or phases are mixed, thereby effecting the change in the acid-sensitive material.

In addition to the two aforementioned layers containing the superacid precursor, secondary acid generator and acid-sensitive material, the imaging media of the present invention may comprise a support and additional layers, for example, a subbing layer to improve adhesion to the support, interlayers for thermally insulating multiple imaging layers from one another, an anti-abrasive topcoat layer, and other auxiliary layers.

The support employed may be transparent or opaque and may be any material that retains its dimensional stability at the temperature used during the heating step. Suitable supports include paper, paper coated with a resin or pigment, such as, calcium carbonate or calcined clay, synthetic papers or plastic films, such as polyethylene, polypropylene, polycarbonate, cellulose acetate and polystyrene. The preferred material for the support is a polyester, desirably poly(ethylene terephthalate).

Usually the layer or layers containing the superacid precursor, secondary acid generator and acid-sensitive material will also contain a binder; typically this layer or these layers are formed by combining the active materials and the binder in a common solvent, applying a layer of the coating composition to the support and then drying. Rather than a solution coating, the layer may be applied as a dispersion or an emulsion. The coating composition also may contain dispersing agents, plasticizers, defoaming agents, coating aids and materials such as waxes to prevent sticking.

The binder used for the layer(s) in which superacid is to be generated must of course be non-basic, such that the superacid is not buffered by the binder. Examples of binders that may be used include methyl cellulose, cellulose acetate butyrate, styrene-acrylonitrile copolymers, polystyrene, poly($\alpha$-methylstyrene), copolymers of styrene and butadiene, poly(methyl methacrylate), copolymers of methyl and ethyl acrylate, poly(vinyl acetate), poly(vinyl butyral), polycarbonate poly(vinylidene chloride) and poly(vinyl chloride). It will be appreciated that the binder selected should not have any adverse effect on the superacid precursor, secondary acid generator or the acid-sensitive material incorporated therein. Also, the binder should be heat-stable at the temperatures encountered during the heating step and should be transparent so that it does not interfere with Viewing of the image. The binder must of course transmit the actinic radiation used to expose the medium.

In forming the layer containing the secondary acid generator, temperatures should be maintained below levels that will initiate thermal decomposition of the secondary acid generator so that the acid-sensitive material will not be prematurely colored or bleached.

The squaric acid derivatives preferred for use in the processes of the present invention can be prepared by known methods, such as those described in U.S. Pat. No. 4,092,146 and Tetrahedron Letters (1977), 4437–38, and 23, 361–4, and Chem. Ber. 121, 569–71 (1988) and 113, 1–8 (1980). In general, the diesters of Formula II can be prepared by reacting disilver squarate with the appropriate alkyl halide(s), preferably the alkyl bromides. The ester groupings may be varied by routine transesterification reactions, or by reacting the diacid chloride of squaric acid with an appropriate alcohol or alkoxide.

Figure 1:
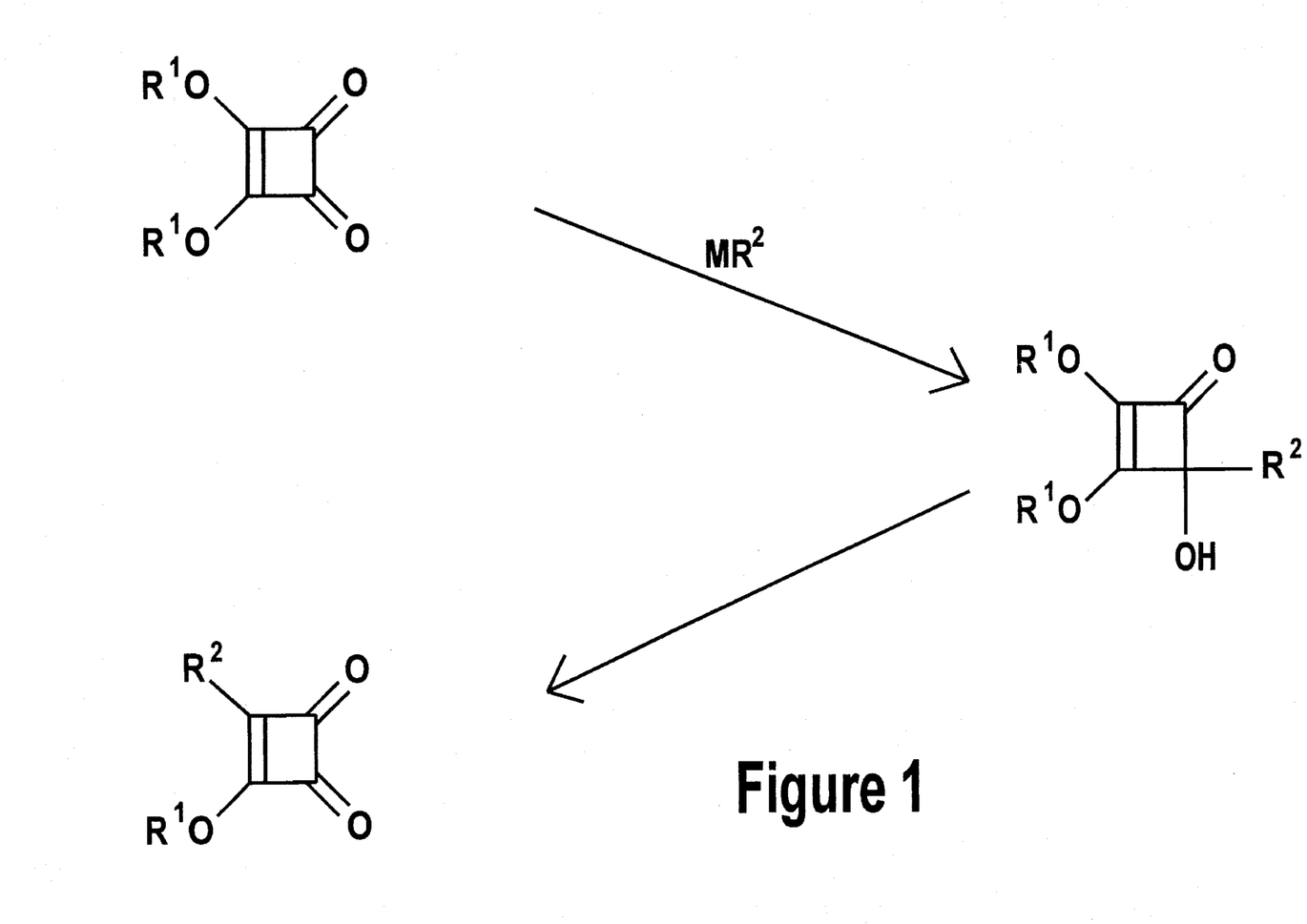
FIG. 1 of the accompanying drawings shows a synthesis of a squaric acid derivative of Formula I below.

The squaric acid derivatives of Formula I in which $R^2$ is an alkyl, cycloalkyl, aralkyl or aryl group can be prepared from derivatives of Formula II by the synthesis shown in FIG. 1. The diester of Formula II is first condensed with a compound containing a negatively charged species $R^2$; this compound is normally an organometallic compound, and preferably an organolithium compound. The reaction adds the —$R^1$ group to one of the oxo groups of the diester to produce the squaric acid derivative of Formula VI; to avoid disubstitution into both oxo groups, not more than the stoichiometric amount of the organometallic reagent should be used.

After being separated from unreacted starting material and other by-products, the squaric acid derivative VI is treated with an acid, for example hydrochloric acid, to convert it to the desired squaric acid derivative I. Although it is possible to simply add acid to the reaction mixture resulting from the treatment of the diester with the organometallic reagent, this course is not recommended, since the squaric acid derivative I produced may be contaminated with unreacted diester, and the diester and squaric acid derivative I are so similar that it is extremely difficult to separate them, even by chromatography.

It will be appreciated that the synthesis shown in FIG. 1 may be modified in various ways. If, for example, the nature of the group $R^1$ desired in the final compound of Formula I is such that it would react with the organometallic reagent, the reactions shown in FIG. 1 may be carried out with a diester in which the ester groupings do not contain the group $R^1$, and the final product of Formula I may be subjected to transesterification or other reactions to introduce the group $R^1$.

The derivatives of Formula I in which $R^2$ is an amino, alkylamino or dialkylamino group can be prepared by similar methods from squaric acid diesters. For example, as illustrated in the Examples below, reaction of bis(4-vinylbenzyl) squarate with methylamine gives 3-amino-4-(p-vinylbenzyloxy)cyclobut-3-ene-1,2-dione. Analogous methods for the synthesis of the other compounds of Formula I will readily be apparent to those skilled in the art of organic synthesis.

The forms of the squaric acid derivative of Formulae I and II in which at least one of $R^1$, $R^2$ and $R^3$ is attached to a polymer may be prepared by reactions analogous to those used to prepare the monomeric derivatives of Formulae I and II, for example by treating a polymer containing appropriate alkoxide groups with the diacid chloride or a monoester monoacid chloride of squaric acid. Alternatively, these polymer-attached derivatives may be prepared by transesterification, for example by treating a polymer containing esterified hydroxyl groups with a monomeric squaric acid derivative of Formula I or II. Other methods for attachment of these derivatives to polymers, or inclusion of these derivatives into polymer backbones, have already been discussed above.

The derivatives of Formula III may be prepared by transesterification from derivatives of Formula II, or another squaric acid diester, and the appropriate diol.

The monomeric oxalic acid derivatives useful in the present process can be prepared by routine esterification techniques which will be familiar to those skilled in organic synthesis, and several Examples of such techniques are exemplified in detail below. The preparation of polymeric oxalic acid derivatives has already been discussed.

Figure 2:
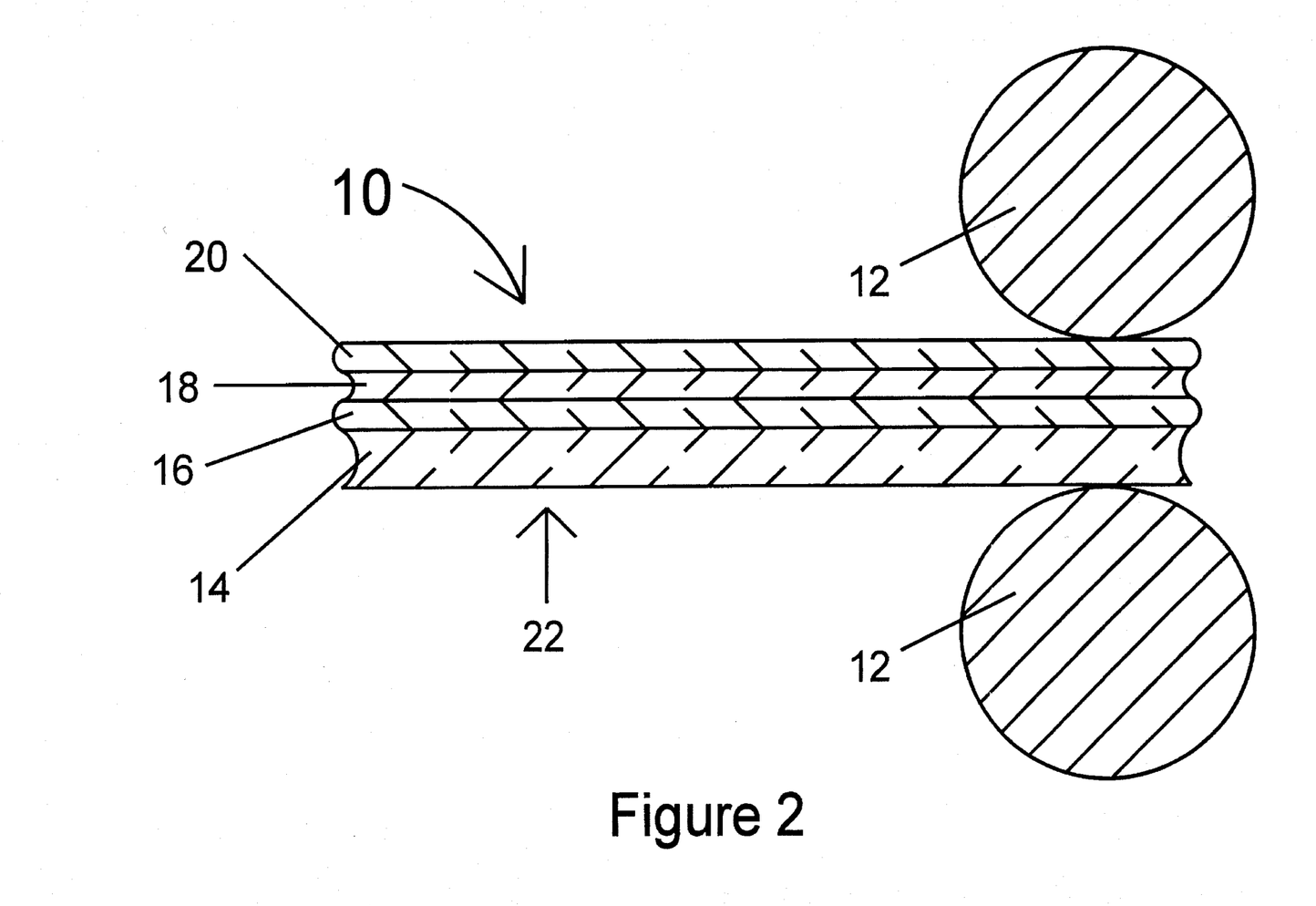
FIG. 2 is a schematic cross-section through an imaging medium of the present invention as it is being passed between a pair of hot rollers during the imaging process of the present invention.

A preferred embodiment of the invention will now be described, though by way of illustration only, with reference to FIG. 2 of the accompanying drawings, which shows a schematic cross-section through an imaging medium (generally designated 10) of the invention as the image therein is being fixed by being passed between a pair of hot rollers 12.

The imaging medium 10 comprises a support 14 formed from a plastic film. Typically the support 14 will comprise a polyethylene terephthalate film 3 to 10 mils (76 to 254 mµ) in thickness, and its upper surface (in FIG. 2) may be treated with a sub-coat, such as is well-known to those skilled in the preparation of imaging media, to improve adhesion of the other layers to the support.

On the support 14 is disposed an acid-forming layer 16 comprising a superacid precursor and a secondary acid generator from which a secondary acid can be liberated by a superacid. The acid-forming layer 16 may also contain a small amount of a basic material to neutralize any acid produced by breakdown of the superacid precursor or secondary acid generator prior to exposure of the medium. On the opposed side of the acid-forming layer 16 from the support 14 is disposed an imaging layer 18 comprising an acid-sensitive material, which changes color in the presence of secondary acid, and a small amount of a base, which serves to neutralize any acid produced by breakdown of the superacid precursor in the acid-forming layer 16. The acid-forming layer 16 and the imaging layer 18 both contain a binder having a glass transition temperature substantially above room temperature.

Finally, the imaging medium comprises an abrasion-resistant topcoat 20.

The imaging medium 10 may be formed by coating the layers 16, 18 and 20 on to the support 14. Alternatively, for example, the layers 16 and 18 may be coated on to the support 14, and the topcoat 20 laminated on to the resultant structure.

The imaging medium 10 is exposed by writing on selected areas of the medium with an ultra-violet laser or using incoherent ultra-violet radiation with exposure being effected through a mask; the exposure of the medium 10 may be effected through the topcoat 20, as indicated by the arrow 22 in the drawing. Within the exposed regions of the acid-forming layer 16, the exposure to ultra-violet radiation causes breakdown of the superacid precursor with the formation of the corresponding superacid. After exposure, the imaging medium 10 is passed between the heated rollers 12. The heat and pressure applied by the rollers 12 causes the superacid present in the exposed regions of the acid-forming layer 16 to bring about catalytic breakdown of the secondary acid generator therein, thereby causing formation of a quantity of secondary acid substantially larger than the quantity of superacid originally generated by the ultra-violet radiation. The heat and pressure applied by the rollers 12 also heats the color-forming layer 18 and the acid-forming layer 16 above their glass transition temperatures, thereby causing the diffusible components of these two layers to become intermixed so that, in exposed regions, the acid produced in the acid-forming layer 16 effects the color change of the acid-sensitive material, thereby forming an image.

The following Examples are now given, though by way of illustration only, to show details of preferred reagents, conditions and techniques used in the process and imaging medium of the present invention.

EXAMPLES 1–11

Preparation of Squaric Acid Derivative Secondary Acid Generators 3,4-Bis(t-butoxy)cyclobut-3-ene-1,2-dione ("bis t-butyl squarate"; hereinafter referred to as "Compound A") used in certain Examples below was prepared as described in E. V. Dehmlow et al., Chem. Ber. 113, 1–8 (1980). 3,4-Bis(benzyloxy)cyclobut-3-ene-1,2-dione ("dibenzyl squarate"; hereinafter referred to as "Compound B") used in certain Examples below was prepared as described in N. Islam et al, Tetrahedron 43, 959–970 (1987). Silver squarate was prepared as described in S. Cohen et al., J. Am. Chem. Soc., 88, 5433 (1966).

EXAMPLE 1

Preparation of bis(3-bromo-2,3-dimethylbut-2-yl) squarate

This Example illustrates the preparation of 3,4-bis(3-bromo-2,3-dimethylbut-2-oxy)-cyclobut-3-ene-1,2-dione ("bis(3-bromo-2,3-dimethylbut-2-yl) squarate"), the compound of Formula II in which $R^1$ and $R^3$ are each a 3-bromo-2,3-dimethylbut-2-yl group.

Silver squarate (1.0 g, 3.0 mmole) was added to a solution of 2,3-dibromo-2,3-dimethylbutane (1.0 g, 4.0 mmole) in dry ether (3 mL) at room temperature. The suspension became warm, and was cooled by a water bath at room temperature. After six hours' stirring, the precipitate remaining was removed by filtration, and washed with ether. The combined ether extracts were concentrated, and the crude product obtained therefrom was purified by flash chromatography on silica gel with 1:3 ether/hexanes as eluent to give the diester (140 mg, 11% yield) as a white powder which decomposed at 131°–132° C. The structure of the compound was confirmed by mass spectroscopy and by $^1H$ and $^{13}C$ NMR spectroscopy.

EXAMPLE 2

Preparation of
3-t-butoxy-4-phenylcyclobut-3-ene-1,2-dione

This Example illustrates the preparation of 3-t-butoxy-4-phenylcyclobut- 3-ene-1,2-dione, the compound of Formula I in which $R^1$ is a tertiary butyl group and $R^2$ is a phenyl group.

Phenyl magnesium bromide (4.6 mL of a 1.0M solution in THF, 4.6 mmole) was added dropwise over a period of 5 minutes to a solution of di-t-butyl squarate (1.0 g, 4.42 mmole) in dry ether (10 mL) at −78° C. under nitrogen. After 30 minutes, the reaction mixture was warmed to 0° C., and stirred at this temperature for an additional one hour. Water (10 mL) and ether (10 mL) were then added to the reaction mixture and the layers were separated. The aqueous layer was extracted twice with dichloromethane. The combined organic layers were dried over magnesium sulfate and concentrated, to give a yellow oil (1.43 g), which crystallized. The resultant material was dissolved in dichloromethane (25 mL) and concentrated hydrochloric acid (4 drops) was added, with stirring, to this solution at room temperature. After 30 minutes, a further four drops of concentrated hydrochloric acid were added. Dichloromethane (25 mL) was added, and the resultant solution was washed with a saturated solution of sodium bicarbonate and then with brine, dried over magnesium sulfate, and concentrated. The crude product thus obtained was purified by flash chromatography on silica gel with toluene as eluent. The chromatographed material was further purified by recrystallization from toluene/hexanes to give the desired monoester as yellow crystals (142 mg, 14% yield) which decomposed at 105°–110° C. The structure of this compound was confirmed by mass spectroscopy and by $^1$H and $^{13}$C NMR spectroscopy.

EXAMPLE 3

Preparation of
3,4-bis(α-methylbenzyloxy)-cyclobut-3-ene-1,2-dione

This Example illustrates the preparation of 3,4-bis(α-methylbenzyloxy)-cyclobut- 3-ene-1,2-dione ("bis(α-methylbenzyl) squarate"; hereinafter referred to as "Compound C"), the compound of Formula II in which $R^1$ and $R^3$ are each an α-methylbenzyl group.

1-Bromo-1-phenylethane (3.1 g, 16.8 mmole) was added dropwise to a suspension of silver squarate (2.5 g, 7.62 mmole) in dry ether (40 mL) at 0° C. After the addition was complete, the reaction mixture was allowed to warm to room temperature and was stirred for four hours in the dark. The solid remaining after this time (silver bromide) was removed by filtration and washed with more ether. The combined ether solutions were washed with a saturated solution of sodium bicarbonate and dried over sodium sulfate. Evaporation of the solvent was followed by purification by flash chromatography on silica gel with 0–60% ether/hexanes as eluant to give the desired diester (394 mg, 16% yield) as a colorless oil. The diester was obtained as a mixture of diastereoisomers which were not separable by this type of chromatography. The structure of the diester was confirmed by mass spectroscopy and by $^1$H and $^{13}$C NMR spectroscopy.

EXAMPLE 4

Preparation of
3,4-bis(p-methylbenzyloxy)-cyclobut-3-ene-1,2-dione

This Example illustrates the preparation of 3,4-bis(p-methylbenzyloxy)-cyclobut- 3-ene-1,2-dione ("bis(p-methylbenzyl) squarate", hereinafter called "Compound D"), the compound of Formula II in which $R^1$ and $R^3$ are each a p-methylbenzyl group.

Triethylamine (0.93 g, 9.2 mmole) was added to a stirred suspension of squaric acid (0.5 g, 4.38 mmole) in chloroform (10 mL) and the resultant solution was cooled with an ice/water bath. A solution of α-bromo-p-xylene (2.03 g, 11.0 mmole) in chloroform (10 mL) was then added dropwise over a period of 30 minutes. After this time, the cooling bath was removed and the solution was held at room temperature for 4.5 hours. The reaction mixture was then diluted with chloroform (20 mL), washed successively with a saturated aqueous solution of sodium bicarbonate (2×20 mL) and saturated brine (20 mL), dried over magnesium sulfate and concentrated under reduced pressure. The resultant oil was further purified by partition between ether (50 mL) and saturated aqueous sodium bicarbonate (20 mL) and separation of the organic layer. The organic layer was washed successively with a saturated aqueous solution of sodium bicarbonate (20 mL) and saturated brine (20 mL), dried over magnesium sulfate and concentrated under reduced pressure. The oil which resulted was crystallized from hot hexanes (20 mL) to give the desired compound (300 mg, 21.3% yield) as off-white crystals. The structure of this compound was confirmed by mass spectroscopy and by $^1$H and $^{13}$C NMR spectroscopy.

EXAMPLE 5

Preparation of
3,4-bis(cyclohexyloxy)-cyclobut-3-ene-1,2-dione

This Example illustrates the preparation of 3,4-bis(cyclohexyloxy)-cyclobut- 3-ene-1,2-dione ("dicyclohexyl squarate", hereinafter called "Compound E"), the compound of Formula II in which $R^1$ and $R^3$ are each a cyclohexyl group.

Cyclohexyl bromide (9.95 g, 61 mmole) was added dropwise over a period of 20 minutes to a stirred suspension of silver squarate (4.0 g, 12.2 mmole) in ether (80 mL) in the dark with ice/water cooling. The ice bath was then removed and the reaction mixture was stirred overnight at room temperature, then filtered to remove silver bromide, and the residue was washed with ether (2×20 mL). The ether solutions were combined and washed successively with a saturated aqueous solution of sodium bicarbonate (50 mL) and saturated brine (50 mL), dried over magnesium sulfate and concentrated under reduced pressure to give the desired compound as a viscous oil which solidified upon storage in a refrigerator to give an off-white solid (0.55 g, 16% yield). The structure of this compound was confirmed by mass spectroscopy and by $^1$H and $^{13}$C NMR spectroscopy.

EXAMPLE 6

Preparation of
3-amino-4-(t-butoxy)-cyclobut-3-ene-1,2-dione

This Example illustrates the preparation of 3-amino-4-(t-butoxy)-cyclobut- 3-ene-1,2-dione (hereinafter called "Compound F"), the compound of Formula I in which $R^1$ is a tertiary butyl group and $R^2$ is an amino group.

A stream of ammonia gas was passed into a stirred solution of Compound A (0.7 g, 3.07 mmole) in methanol (40 mL) for 2 minutes. The solution was then allowed to stand at room temperature for 1 hour, during which time a small amount of insoluble material was precipitated. The sediment was removed by filtration, and the solvent was removed under reduced pressure to yield a yellow solid, which was washed with ether (2×50 mL) to remove starting material and butanol (0.16 g of impurities were collected, after solvent evaporation). The solid which remained was dissolved in dichloromethane (150 mL) and the solution was filtered. Removal of the solvent under reduced pressure yielded the desired compound as white crystals (0.25 g, 48% yield) which melted at 220°–225° C. The structure of this compound was confirmed by $^1$H NMR spectroscopy.

EXAMPLE 7

Preparation of 4-hexyl-3-(p-vinyl-benzyloxy)cyclobut-3-ene-1,2-dione

This Example illustrates the preparation of 4-hexyl-3-(p-vinylbenzyloxy)-cyclobut- 3-ene-1,2-dione (hereinafter called "Compound G"), the compound of Formula I in which $R^2$ is a hexyl group and $R^1$ is an p-vinylbenzyl group.
Part A: Preparation of 2,3-dibutoxy-4-hexyl-4-hydroxycyclobut-2-en- 1-one Hexyl magnesium bromide (40 mL of a 2M solution in ether, 80.0 mmole) was added dropwise over a period of 45 minutes to a solution of di-n-butyl squarate in dry THF (150 mL) at −78° C. under nitrogen, and the reaction mixture was held at that temperature for 1 hour. The reaction mixture was then allowed to warm to room temperature are stirred for an additional 3 hours, after which time it was cooled using an ice/water bath, and quenched by the addition of water (25 mL) added dropwise over a period of 5 minutes. Saturated brine (300 mL) and ether (300 mL) were then added, the layers were separated, and the aqueous layer was extracted with additional ether (300 mL). The ether extracts were combined and dried over magnesium sulfate, and the solvents were removed to give a golden oil (15.64 g) containing the desired product; this oil was used without further purification in Part B below.
Part B: Preparation of 3-hexyl-4-hydroxy-cyclobut-3-ene-1,2-dione 6N Hydrochloric acid (150 mL) was added in one portion to a stirred solution of crude 2,3-dibutoxy-4-hexyl-4-hydroxycyclobut-2-en-1-one (15.1 g, prepared in Part A above) in THF (150 mL), and the resultant solution was stirred at room temperature for 3 hours. The reaction mixture was then concentrated under reduced pressure to give a yellow solid. To this solid was added water (100 mL), which was then removed under reduced pressure. Toluene (100 mL) was similarly added and removed under reduced pressure, and then dichloromethane (200 mL) was added to the residue and the resultant solution was filtered and concentrated to produce a yellow oil. Hexanes (200 mL) were added and the resultant solution was cooled to induce crystallization. After recrystallization from hexanes, the desired compound was isolated as tan crystals (4.28 g, 33% yield over Parts A and B). The structure of this compound was confirmed by mass spectroscopy and by $^1$H and $^{13}$C NMR spectroscopy.
Part C: Preparation of 4-hexyl-3-(p-vinylbenzyloxy)-cyclobut-3-ene- 1,2-dione Triethylamine (1.75 g, 17.3 mmole), 2,6-di-t-butyl-4-methylphenol (a radical inhibitor, 0.7 mg, 3.4 μmol) and 4-vinylbenzyl chloride (5.04 g, 33 mmole) were added, in that order, to a solution of 3-hexyl-4-hydroxy-cyclobut-3-en-1,2-one (3.0 g, 16.5 mmole, prepared in Part B above) in chloroform (90 mL), and the resultant solution was heated at reflux for 7 hours. The solution was then cooled and allowed to stand overnight at room temperature, after which it was heated at reflux for a further 7 hours, then cooled and allowed to stand overnight a second time. The reaction mixture was then concentrated under reduced pressure, the residue dissolved in dichloromethane (150 mL), and the resultant solution washed with water (2×75 mL), dried over magnesium sulfate and concentrated under reduced pressure to yield a yellow oil, which was purified by short-path distillation (to remove excess 4-vinylbenzyl chloride) at 72°–74° C. and 1.7 mm Hg pressure. The residue from the distillation was purified by flash chromatography on silica gel with dichloromethane as eluant to give the desired compound (1.23 g, 25% yield) as a golden oil. The structure of this compound was confirmed by mass spectroscopy and by $^1$H and $^{13}$C NMR spectroscopy.

EXAMPLE 8

Preparation of 3-methylamino-4-(p-vinyl-benzyloxy)cyclobut-3-ene-1,2-dione

This Example illustrates the preparation of 3-methylamino-4-(p-vinylbenzyloxy)-cyclobut- 3-ene-1,2-dione (hereinafter referred to as "Compound H"), the compound of Formula I in which $R^2$ is an amino group and $R^1$ is a p-vinylbenzyl group.
Part A: Preparation of bis(4-vinylbenzyl) squarate 4-Vinylbenzyl chloride (13 g, 85 mmole) was added to a suspension of silver squarate (5.5 g, 48 mmole) in dry ether (100 mL), and the resultant mixture was stirred in the dark for 3 days. The reaction mixture was then filtered and the solvent removed under reduced pressure. The residue was taken up in dichloromethane and filtered through a short column of silica gel, then concentrated under reduced pressure, to yield the desired compound in a crude form, which was used in Part B below without further purification.
Part B: Preparation of 3-methylamino-4-(p-vinylbenzyloxy)-cyclobut- 3-ene-1,2-dione The crude product from Part A above was dissolved in ether (300 mL) and gaseous methylamine was bubbled through this ether solution for 1 minute. The resultant mixture was allowed to stand for 5 minutes, then the precipitate which had formed was removed by filtration, redissolved in chloroform and filtered through Celite (manufactured by Johns-Manville Corporation, Denver, Colo. 80217). The solvent was removed under reduced pressure to give the desired product (hereinafter called "Compound H") as a white solid, melting point 152° C. (3.5 g, 30% yield over Parts A and B). The structure of this compound was confirmed by $^1$H NMR spectroscopy.

EXAMPLE 9

Preparation of copolymer of Compound H with lauryl methacrylate

This Example illustrates the preparation of a 1:1 w/w copolymer of Compound H prepared in Example 8 above with lauryl methacrylate.

Compound H (1 g) and lauryl methacrylate (1 g) were dissolved in a mixture of 2-propanol (30 mL) and ethanol (20 mL), and the resultant solution was purged with nitrogen. Azoisobutyronitrile (0.01 g) was then added, and the solution was held at 65° C. overnight, during which time a precipitate (250 mg) formed. This precipitate was collected and shown by infra-red spectroscopy to contain squarate esters.

EXAMPLE 10

Preparation of 4-[5-[1,2-dioxo-3-hydroxycyclobut-3-en-4-yl]pent-1-yl]- 3-hydroxycyclobut-3-ene-1,2-dione Pentamethylenebis(magnesium bromide) (25 mL of a 0.5M solution in THF, 12.5 mmole) was added dropwise over a period of 15 minutes to a solution of dibutyl squarate (5.66 g, 25 mmole) in dry THF (50 mL) at −78° C. under a stream of nitrogen. The resulting suspension was stirred at −78° C. for 1 hour, then allowed to warm to room temperature and stirred for a further 2 hours. The homogeneous yellow solution which resulted was cooled to 0° C., and water (10 mL) was added dropwise over a period of 2 minutes. After standing for 5 minutes, the solution was diluted with THF (50 mL) and washed with saturated sodium chloride solution (150 mL). An emulsion was formed, which was separated by evaporative removal of THF and addition of dichloromethane (200 mL). The organic layer was separated and the aqueous layer was extracted with more dichloromethane (100 mL). The combined dichloromethane layers were dried over magnesium sulfate and concentrated under reduced pressure to yield a golden oil which was shown by thin layer chromatography, on silica gel with 1:1 ether/hexanes as eluent, to consist of five components.

This mixture was separated by flash chromatography on silica gel with 1:1 ether/hexanes, followed by pure ether, as eluents. Each of the five components was examined by $^1$H NMR spectroscopy. The third and fourth components (in order of elution from the column) were tentatively assigned as 4-[5-[1,2-dioxo-3-butoxycyclobut- 3-en-4-yl]pent-1-yl]-3-butoxycyclobut-3-ene-1,2-dione (0.69 g) and 2,3-dibutoxy-4-[5-[1,2-dioxo-3-butoxycyclobut-3-en-4-yl]pent-1-yl]-4 -hydroxycyclobut-2-en-1-one (2.14 g).

A portion of the isolated fourth component (2.01 g) was dissolved in THF (20 mL), and the resultant solution was treated with 6M hydrochloric acid (20 mL). The two-phase mixture became warm, and after 15 minutes stirring was observed to have become homogeneous. After a further two hours stirring, the solution was concentrated to dryness under reduced pressure. Water (20 mL) was added, and removed by evaporation, in order to drive off excess hydrogen chloride. The remaining water was removed by azeotropic distillation under reduced pressure with dichloromethane/acetone, to yield an off-white solid. This material was purified by recrystallization from THF/ether to yield the desired compound as a tan powder (542 mg, 18% yield over two steps). The structure of this compound was confirmed by $^1$H and $^{13}$C NMR spectroscopy.

EXAMPLE 11

Preparation of 4-[5-[1,2-dioxo-3-[4-methyl-benzyloxy]cyclobut-3-en-4-yl]pent-1-yl]-3-[4-methylbenzyloxy]cyclobut-3-ene-1,2-dione This Example illustrates the preparation of a dimeric squaric acid derivative in which two [4-methylbenzyloxy] cyclobut-3-ene-1,2-dione groups are linked via a pentamethylene chain.

Triethylamine (423 mg, 4.18 mmole) and p-methylbenzyl bromide (1.47 g, 7.96 mmole) were added sequentially to a suspension of 4-[5-[1,2-dioxo- 3-hydroxycyclobut-3-en-4-yl]pent-1-yl]-3-hydroxy-cyclobut-3-ene-1,2-dione (526 mg, 2.0 mmole, prepared in Example 10 above) in chloroform (15 mL) at room temperature, and the mixture was then heated at reflux for 9 hours. The solvent was removed under reduced pressure, and the resultant oil was purified by flash chromatography on silica gel with dichloromethane, followed by ether, as eluents. The product eluted with ether, and was obtained as a yellow oil (591 mg, 63% yield). The structure of this compound was confirmed by $^1$H and $^{13}$C NMR spectroscopy.

EXAMPLES 12–32

Preparation of Oxalic Acid Derivative Secondary Acid Generators

EXAMPLE 12

Preparation of bis(2-methyl-2-hexyl) oxalate

To a solution of 2-methylhexan-2-ol (4.65 g, 40 mmole) and pyridine (4.74 g, 60 mmole) in tetrahydrofuran (15 mL) was added dropwise at 5°–10° C. over a period of 15 minutes a solution of oxalyl chloride (2.54 g, 20 mmole) in THF (6 mL). The resultant suspension was stirred at 20° C. overnight, then diluted with cold water (100 mL) and extracted with diethyl ether (65 mL). The organic layer was washed with cold dilute sulfuric acid, then with aqueous sodium bicarbonate, and finally with aqueous sodium chloride, then dried over sodium sulfate and evaporated to give the desired product as a pale yellow oil (3.25 g, 62% yield). An analytical sample was obtained by column chromatography on silica gel with 7% ethyl acetate in hexanes as eluent. The structure of this compound was confirmed by mass spectroscopy and by $^1$H and $^{13}$C NMR spectroscopy.

EXAMPLE 13

Preparation of bis(α,α-dimethylbenzyl) oxalate

To a solution of α,α-dimethylbenzyl alcohol (5.44 g, 40 mmole) and pyridine (4.74 g) in THF (20 mL) was added dropwise at 5°–10° C. with stirring over a period of 25 minutes a solution of oxalyl chloride (2.54 g, 20 mmole) in THF (5 mL). The resultant suspension was stirred at 20° C. for 5 hrs, then poured into 140 mL of 0.5N sulfuric acid kept at 0° C. The oily product which separated was extracted with diethyl ether (60 mL) and the ether solution washed with saturated sodium bicarbonate (50 mL), and then with saturated aqueous sodium chloride (50 mL). The washed solution was dried over sodium sulfate and evaporated to give the desired product as a nearly colorless solid (5.745 g, 88% crude yield). A portion of this product was recrystallized from hexanes to provide colorless needles melting point 76.5°–79° C. The structure of this compound was confirmed by mass spectroscopy and by $^1$H and $^{13}$C NMR spectroscopy.

EXAMPLE 14

Preparation of bis(p-butoxybenzyl) oxalate

To a solution of p-butoxybenzyl alcohol (1.803 g, 10 mmole) and pyridine (1.185 g, 15 mmole) in dichloromethane (10 mL) was added dropwise over a period of 5 minutes a solution of oxalyl chloride (0.635 g, 5 mmole) in methylene chloride (7 mL) at a temperature of 5°–20° C. The resultant suspension was stirred at 20° C. overnight, diluted to 50 mL with methylene chloride, then washed successively with water, dilute sulfuric acid, and aqueous sodium bicarbonate, and finally with brine. The washed suspension was then dried over sodium sulfate and evaporated to give the desired product (1.97 g, 76% yield) as colorless plates, melting point 113.5°–114.5° C. The structure of this compound was confirmed by mass spectroscopy and by $^1$H and $^{13}$C NMR spectroscopy.

EXAMPLE 15

Preparation of bis(α-methylbenzyl) oxalate

To a solution of d,l-α-methylbenzyl alcohol (2.443 g, 20 mmole) and pyridine (2.37 g, 30 mmole) in dichloromethane (20 mL) was added at 5° C. a solution of oxalyl chloride (1.27 g, 10 mmole) in dichloromethane (8 mL). The resultant suspension was stirred at 0° C. for 20 minutes, and then at 20° C. overnight. The suspension was then poured into ice-water and acidified with 1N sulfuric acid (20 mL). The organic layer was washed with dilute sodium bicarbonate solution, then with brine, dried over sodium sulfate and evaporated to give the desired product as a pale yellow oil (2.661 g, 89% yield). The structure of this compound was confirmed by mass spectroscopy and by $^1$H and $^{13}$C NMR spectroscopy.

EXAMPLE 16

Preparation of bis(p-methoxy-α-methylbenzyl) oxalate

To a solution of d,l-p-methoxy-α-phenethyl alcohol (3.57 g, 23.4 mmole) in dichloromethane (35 mL) containing 2.78 g (35.8 mmole) of pyridine was added over a period of 20 minutes at 0° C. a solution of oxalyl chloride (1.49 g, 11.8 mmole) in dichloromethane (6 mL). The resultant mixture was stirred at 20° C. for 14 hours, then poured into cold dilute sulfuric acid. The organic layer was washed with cold water, then with dilute sodium bicarbonate, dried over sodium sulfate and evaporated to give the desired product as a colorless oil (4.11 g, 97% yield). A 1.2 gram sample of this oil was crystallized from methanol to provide 0.51 g of product as fine matted plates of a mixture of diastereomers melting at 63°–82° C. The structure of this compound was confirmed by mass spectroscopy and by $^1$H and $^{13}$C NMR spectroscopy.

EXAMPLE 17

Preparation of bis(p-methylbenzyl) oxalate

To a solution of p-methylbenzyl alcohol (3.33 g, 27 mmole) in pyridine (7 mL) was added at 0° C. over a period of five minutes oxalyl chloride (0.87 mL, 1.27 g, 10 mmole). The resultant reaction mixture was stirred at 0°–10° C. for one hour, then poured into cold dilute sulfuric acid to give a colorless precipitate, which was collected by filtration and washed with cold water to give colorless plates. These plates were recrystallized from methanol and then from hexanes as matted needles. The needles were recrystallized from methanol (30 mL) to provide the desired product (0.96 g, 32% yield), melting point 100°–100.5° C. A second crop of the product (1.20 g, 40% yield) was obtained by concentration of the mother liquors. The structure of the product was confirmed by mass spectroscopy and by $^1$H and $^{13}$C NMR spectroscopy.

EXAMPLE 18

Preparation of ethyl p-methoxybenzyl oxalate

To a solution of p-methoxybenzyl alcohol (4.49 g, 14.4 mmole) and pyridine (1.92 g, 24.3 mmole) in dichloromethane (10 mL) was added at 5°–20° C. a solution of ethyl oxalyl chloride (2.216 g, 16.2 mmole) over a period of 4 minutes. The resultant reaction mixture was stirred at 0° C. for 20 minutes and then at 20° C. overnight. The reaction mixture was then poured into ice-water and acidified with 1N sulfuric acid (20 mL). The organic layer was washed with dilute sodium bicarbonate, then with brine, dried over sodium sulfate and evaporated to give the desired product (3.367 g) as a colorless solid. Recrystallization from hexanes provided colorless fine irregular prisms, melting point 44°–45° C. The structure of this compound was confirmed by mass spectroscopy and by $^1$H and $^{13}$C NMR spectroscopy.

EXAMPLE 19

Preparation of 2,2-dimethyl-1-[4-methoxybenzyloxalyloxy]prop-3-yl [4-methoxybenzyl]oxalate A solution of 2,2-dimethylpropane-1,3-diol (24.6 g, 0.236 mole) in dichloromethane (200 mL) was added in a slow stream to a solution of oxalyl chloride (60.0 g, 0.472 mole) in dichloromethane (400 mL) which had been precooled to 0° C. using an ice bath, the addition being made at such a rate that the temperature of the solution did not exceed 10° C. The resultant clear solution was allowed to warm to room temperature over a period of 30 minutes, and stirred for an additional 30 minutes, then cooled to 0° C. and pyridine (75 g, 0.948 mole) was added, again at such a rate as to maintain the temperature of the reaction mixture below 10° C. To the resultant yellow suspension was added a solution of 4-methoxybenzyl alcohol (65.35 g, 0.473 mole) in dichloromethane (100 mL), again keeping the temperature of the reaction mixture to 10° C. or below. After the addition had been completed, a cream-colored precipitate was observed. The reaction mixture was allowed to warm to room temperature and stirred overnight.

The mixture was then filtered, and the hygroscopic precipitate of pyridinium chloride was washed with dichloromethane (2×25 mL). The combined organic extracts were washed with: a) water (500 mL) containing concentrated hydrochloric acid (25 mL); b) water (700 mL) containing sodium hydrogen carbonate (50 g) and c) saturated brine (250 mL). The organic layer was then dried over anhydrous sodium sulfate and concentrated under reduced pressure. The residue was stirred with ether (500 mL) for 10 minutes, then filtered. The precipitate (which was the unwanted by-product, 4-methoxybenzyl oxalate) was washed with more ether (2×25 mL), and the combined ether solutions were concentrated under reduced pressure to give a waxy solid (93.88 g), which resisted attempts at recrystallization. Purification was, however, effected by trituration with cold methanol (500 mL) to afford the desired compound (68.5 g, 59% yield) as a white powder, melting point 38°–40° C. The structure of this compound was confirmed by mass spectroscopy and by $^1$H and $^{13}$C NMR spectroscopy.

EXAMPLE 20

Preparation of 2,2-dimethyl-1-[4-benzyloxy[benzyloxalyloxy]]prop-3-yl [4-methoxybenzyl]oxalate Example 19 was repeated except that the 4-methoxybenzyl alcohol was replaced by 4-benzyloxybenzyl alcohol, to give the above compound in 73% yield. This compound had a melting point of 73°–74° C., and its structure was confirmed by mass spectroscopy and by $^1$H and $^{13}$C NMR spectroscopy.

EXAMPLE 21

Preparation of 1-[4-methoxybenzyloxalyloxy]]hex-6-yl [4-methoxybenzyl]oxalate

Example 19 was repeated except that the 2,2-dimethyl-propane-1,3-diol was replaced by hexane-1,6-diol, to give the above compound in 49% yield. This compound had a melting point of 114°–115° C., and its structure was confirmed by mass spectroscopy and by $^1$H and $^{13}$C NMR spectroscopy.

EXAMPLE 22

Preparation of cyclohexyl [4-[6-[4-[[cyclohexyloxalyloxy]methyl]phenoxy]hex-6-yloxy]benzyl]oxalate Part A: Preparation of 4-[1-[4-hydroxymethylphenoxy] hex-6-yloxy]benzyl alcohol 4-Hydroxybenzyl alcohol (24.82 g, 0.2 mole) was added to a stirred suspension of finely ground potassium carbonate (42.0 g, 0.4 mole) in dry dimethylformamide (250 mL). The resultant mixture was stirred at 60° C. under dry nitrogen for 10 minutes, then 1,6-dibromohexane (24.4 g, 0.1 mole) was added. The reaction mixture was maintained at 60° C. for 5 hours, then allowed to cool to room temperature and stirred for 17 hours. The reaction mixture was then poured slowly into ice/water (800 mL). A tan precipitate formed, which was collected by filtration, washed with water, and dried in air to give a sticky solid. This material was triturated with 2-propanol (100 mL) and then with cold water (200 mL), to give the desired product as a powder (13.8 g, 42% yield) which was collected by (slow and difficult) filtration. The compound melted at 96°–110° C., and its structure was confirmed by mass spectroscopy and by $^1$H and $^{13}$C NMR spectroscopy.

Part B: Preparation of cyclohexyl [4-[6-[4-[[cyclohexyloxalyloxy]methyl]phenoxy]hex-6-yloxy]benzyl]oxalate A solution of cyclohexanol (2.0 g, 0.02 mole) in dichloromethane (50 mL) was added over a period of 15 minutes to a solution of oxalyl chloride (2.54 g, 0.02 mole) in dichloromethane (50 mL) cooled on an ice bath. The resultant solution was allowed to warm to room temperature over a period of 20 minutes, then stirred for a further 30 minutes, then again cooled, using an ice bath, and pyridine (3.16 g, 0.04 mole) was added over a two minute period. After 5 minutes standing, solid 4-[1-[4-hydroxymethylphenoxy] hex-6-yloxy]benzyl alcohol (prepared in Part A above, 3.30 g, 0.01 mole) was added in portions over a period of 15 minutes. The slightly turbid solution which formed was allowed to warm to room temperature and stirred for about 30 hours under nitrogen. This solution was then washed with: a) water (100 mL) containing concentrated hydrochloric acid (10 mL); b) saturated aqueous sodium hydrogen carbonate (100 mL) and c) saturated brine (50 mL). The organic layer was then dried over anhydrous sodium sulfate. Charcoal and Celite were added, and the solution was then filtered through Celite. After concentration of the filtrate under reduced pressure, the residue was purified by flash chromatography on silica gel with dichloromethane as eluent, giving the desired compound as a pale yellow oil (0.65 g, 10% yield). The structure of this compound was confirmed by mass spectroscopy and by $^1$H and $^{13}$C NMR spectroscopy.

EXAMPLE 23

Preparation of adamantyl [4-[6-[4-[[adamantyloxalyloxy]methyl]phenoxy]hex-6-yloxy]benzyl]oxalate Example 22, Part B was repeated except that the cyclohexanol was replaced by an equimolar amount of adamantanol. The above compound was produced as a pale yellow oil in 22% yield, and its structure was confirmed by mass spectroscopy and by $^1$H and $^{13}$C NMR spectroscopy.

EXAMPLE 24

Preparation of Menthyl [4-[6-[4-[[menthyloxalyloxy]methyl]phenoxy]hex-6-yloxy]benzyl]oxalate Example 22, Part B was repeated except that the cyclohexanol was replaced by an equimolar amount of d,l-menthol. The above compound was produced as a pale yellow oil in 22% yield, and its structure was confirmed by mass spectroscopy and by $^1$H and $^{13}$C NMR spectroscopy.

EXAMPLE 25

Preparation of 2-methacryloxyethyl p-methoxybenzyl oxalate

Part A: Preparation of 2-methacryloxyethy oxalyl chloride

Oxalyl chloride (50 g) and dichloromethane (50 g) were mixed and cooled, with stirring, in an ice bath to 7°–10° C. To the resultant mixture was added 2-hydroxyethyl methacrylate (40 g) over a period of 30 minutes. The resultant mixture was stirred overnight at room temperature under a slow stream of nitrogen, then concentrated on a rotary evaporator for one hour to yield the desired product as a colorless oil (65 g), which was sufficiently pure to be used in Part B below without further purification.

Part B: Preparation of 2-methacryloxyethyl p-methoxybenzyl oxalate p-Methoxybenzyl alcohol (14 g, approximately 0.1 mole) and pyridine (11 g, 0.13 mole) were dissolved in dichloromethane (100 mL) and cooled in an ice bath to 2°–4° C. Separately, the product of Part A above (25 g, 0.11 mole) was dissolved in dichloromethane (25 mL) and cooled in an ice bath. The second solution was added gradually to the first over a period of 25 minutes while keeping the temperature at 2°–4° C. The resultant reaction mixture was allowed to stand at room temperature overnight, then filtered then filtered through a plug of silica to remove a low $R_f$ impurity detectable by thin layer chromatography (TLC). The dichloromethane was then removed by evaporation to yield the desired product as a colorless oil (29 g, 91% yield over two stages). TLC with dichloromethane as eluent gave a single spot, $R_f$ 0.45. The structure of the product was confirmed by $^1$H NMR spectroscopy in deuterochloroform, the spectrum being as follows:

δ=7.28 (doublet, 2H); 6.83 (doublet, 2H); 6.05 (singlet, 1H); 5.50 (singlet, 1H); 5.17 (singlet, 2H); 4.43 (triplet, 2H); 4.37 (triplet, 2H); 3.72 (singlet, 3H); and 1.86 (singlet, 3H) ppm.

EXAMPLE 26

Preparation of poly(2-methacryloxyethyl p-methoxybenzyl oxalate)

The product of Example 25 above (29 g) was dissolved in toluene (200 mL) and azobis(isobutyronitrile) (AIBN; 0.3 g) was added. The resultant mixture was heated at 65° C. under nitrogen for 16 hours, additional AIBN (0.2 g) was added, and the mixture was heated under nitrogen for a further 24 hours. A polymeric product precipitated as a swollen gel, from which the supernatant liquor was decanted. The gel was washed repeatedly with diethyl ether, whereupon it deswelled and hardened. The washed polymer was dried in vacuo at 40° C. to yield the desired polymer (26 g, approximately 90% yield) as a non-sticky white solid, glass transition temperature ($T_g$) 65° C., decomposing at 210° C. in the absence of any catalyst.

EXAMPLE 27

Preparation of 4-methacryloxybutyl p-methoxybenzyl oxalate

Example 25 above was repeated, except that 4-hydroxybutyl methacrylate was substituted for 2-hydroxyethyl methacrylate. The product was obtained as a colorless oil (yield 85%) and its structure was confirmed by $^1$H NMR spectroscopy in deuterochloroform, the spectrum being as follows:

δ=7.28 (doublet, 2H); 6.83 (doublet, 2H); 6.05 (singlet, 1H); 5.50 (singlet, 1H); 5.17 (singlet, 2H); 4.23 (triplet, 2H); 4.13 (triplet, 2H); 3.72 (singlet, 3H); 1.86 (singlet, 3H) and 1.72 (multiplet, 4H) ppm.

EXAMPLE 28

Preparation of poly(4-methacryloxybutyl p-methoxybenzyl oxalate)

The product of Example 27 above (5 g) was dissolved in toluene (25 mL) and AIBN (0.025 g) was added. The resultant mixture was heated at 65° C. under nitrogen for 16 hours, and then poured into hexane, whereupon the desired polymeric product precipitated, $T_g$ approximately 50° C., decomposing above 200° C. in the absence of any catalyst.

EXAMPLE 29

Preparation of 4-benzyloxybenzyl 2-methacryloxyethyl oxalate

Example 25, Part B above was repeated, except that 4-benzyloxybenzyl alcohol was substituted for p-methoxybenzyl alcohol. The product was obtained as a white solid, melting point 40°–42° C. (yield 85%) and its structure was confirmed by $^1$H NMR spectroscopy in deuterochloroform, the spectrum being as follows:

δ=7.4 (multiplet, 5H); 7.28 (doublet, 2H); 6.85 (doublet, 2H); 6.07 (singlet, 1H); 5.52 (singlet, 1H); 5.23 (singlet, 2H); 5.02 (singlet, 2H); 4.45 (triplet, 2H); 4.35 (triplet, 2H); and 1.88 (singlet, 3H) ppm.

This monomer was convened to its homopolymer in the same manner as described in Example 28 above.

EXAMPLE 30

Preparation of ethyl 4-(4-vinylbenzyloxy)benzyl oxalate

Part A: Preparation of 4-(4-vinylbenzyloxy)benzyl alcohol

A solution of potassium hydroxide pellets (3.2 g, 0.05 mole) in 50 mL of ethanol was prepared and stirred in a flask under nitrogen. Separately, p-hydroxybenzyl alcohol (6.2 g, 0.05 mole) and p-vinylbenzyl chloride (7.6 g, 0.05 mole) were dissolved in 50 ml of ethanol. The second solution was added to the first with stirring under nitrogen, and the resultant mixture was heated to 65° C. overnight. The reaction mixture was then cooled to room temperature and filtered, and solvent was removed from the filtrate on a rotary evaporator to give a tan solid. This solid was extracted with warm water, filtered off and dried, extracted with petroleum ether, filtered off and finally recrystallized from toluene/hexane to yield the desired product as a colorless solid (6 g, approximately 50% yield), melting point 110°–112° C. Its structure was confirmed by $^1$H NMR spectroscopy in deuterochloroform, the spectrum being as follows:

δ=7.38 (two doublets, J=10 Hz, 4H); 7.23 (doublet, J=10 Hz, 2H); 6.85 (doublet, J=10 Hz, 2H); 6.67 (two doublets, J=10 and 18 Hz, 1H); 5.72 (doublet, J=18 Hz, 1H); 5.21 (doublet, J=10 Hz, 1H); 5.0 (singlet, 2H); 4.57 (singlet, 2H); and 1.6 (singlet, 1H) ppm.

Part B: Preparation of ethyl 4-(4-vinylbenzyloxy)benzyl oxalate

The product of Part A above (4.8 g, 0.02 mole) and pyridine (2.0 g, 0.025 mole) were dissolved in dichloromethane (50 mL) and cooled to 10°–12° C. To this solution was added over a period of 10 minutes a solution of ethyloxalyl chloride (3 g, 0.022 mole) in dichloromethane (5 mL). TLC of the reaction mixture after the addition had been completed indicated that only a trace of the alcohol starting material remained. The reaction mixture was then filtered through a plug of silica to remove the pyridine salt produced, and the filtrate was concentrated to produce the desired produce as white crystals (approximately 90% yield) melting point 93° C. Its structure was confirmed by $^1$H NMR spectroscopy in deuterochloroform, the spectrum being as follows:

δ=7.35 (two doublets, J=10 Hz, 4H); 7.25 (doublet, J=10 Hz, 2H); 6.85 (doublet, J=10 Hz, 2H); 6.67 (two doublets, J=10 and 18 Hz, 1H); 5.72 (doublet, J=18 Hz, 1H); 5.21 (doublet, J=10 Hz, 1H); 5.18 (singlet, 2H); 5.0 (singlet, 2H); 4.27 (quadruplet, J=8 Hz, 2H); and 1.28 (triplet, J=8 Hz, 3H) ppm.

EXAMPLE 31

Preparation of poly(ethyl 4-(4-vinylbenzyloxy)benzyl oxalate)

The product of Example 30 above (approximately 2 g) was dissolved in toluene (25 mL) and AIBN (0.01 g) was added. The resultant mixture was heated at 65° C. under nitrogen for 16 hours. Proton NMR analysis indicated only about 50% polymerization, so additional AIBN (0.015 g) was added, and the mixture was heated at 65° C. under nitrogen for a further 16 hours. The resultant slightly viscous solution was poured into a 1:1 v/v mixture of diethyl ether and petroleum ether to precipitate the polymer, which was then treated with petroleum ether for deswelling. After drying, the desired polymer (approximately 0.7 g) was obtained as an off-white powder. Proton NMR analysis revealed no trace of remaining monomer.

EXAMPLE 32

Preparation of 4-(4-vinylbenzyloxy)benzyl oxalate)

3-Phenylpropyloxalyl chloride was prepared by reacting oxalyl chloride with 3-phenylpropanol in dichloromethane at 10° C. Example 30, Part B was then repeated using the 3-phenylpropyloxalyl chloride in place of ethyloxalyl chloride, to produce the product as fine white crystals, melting point 80° C. (81% yield). Its structure was confirmed by $^1$H NMR spectroscopy in deuterochloroform, the spectrum being as follows:

$\delta$=7.1–7.4 (multiplet, 9H); 7.27 (doublet, 2H); 6.87 (doublet, 2H); 6.67 (two doublets, 1H); 5.72 (doublet, 1H); 5.22 (doublet, 1H); 5.20 (singlet; 2H); 5.03 (singlet, 2H); 4.21 (triplet, 2H); 2.65 (triplet, 2H); and 2.0 (two triplets, 2H) ppm.

Polymerization of this monomer in the same manner as in Example 31 above gave the corresponding polymer in a yield of 75%. This polymer as found to give good results as a secondary acid generator.

Imaging and Other Processes of the Invention

EXAMPLE 33

Acid-Catalyzed Decomposition of Squaric Acid Derivatives

This Example demonstrates that, in the presence of 1 mole percent methanesulfonic acid (a strong acid), various squaric acid derivatives used in the processes and media of the present invention decompose at substantially lower temperatures than the same derivatives do in the absence of this acid, and thus that the thermal breakdown of these squaric acid derivatives is catalyzed by strong acids.

Compounds A, B, D, E and F described above were doped with 1 percent by weight methanesulfonic acid (MSA) by addition of the appropriate amount of a 2 mM solution of the acid in dichloromethane, followed by evaporation of the solvent. The acid-treated materials were compared with the pure compounds using thermal gravimetric analysis (TGA) under a nitrogen atmosphere with a rate of temperature increase of 10° C. per minute. Compounds B and D, whose decompositions did not result in loss of an obvious gaseous by-product, were also examined by differential scanning calorimetry (DSC) under the same conditions of temperature and inert atmosphere. Calculated onset temperatures of decomposition (COTD's), and percent weight loss (for TGA) or heat evolved (for DSC) are shown in Table 1 below.

TABLE 1

| Compound | TGA | | DSC | |
|---|---|---|---|---|
| | CROD, °C. | % loss | CTOD, °C. | Heat, J/g |
| A | 90.9 | 47.5 | — | — |
| A + MSA | 70.0 | 46.8 | — | — |
| B | 199.1 | 14.4 | 179.5 | 503 |
| B + MSA | 181.4 | 10.1 | 166.4 | 459 |
| D | 169.4 | 4.7 | 156.5 | 349 |
| D + MSA | 142.3 | 3.8 | 136.2 | 320 |
| E | 231.3 | 62.7 | — | — |
| E + MSA | 200.6 | 60.4 | — | — |

TABLE 1-continued

| Compound | TGA | | DSC | |
|---|---|---|---|---|
| | CROD, °C. | % loss | CTOD, °C. | Heat, J/g |
| F | 145.3 | 29.9 | — | — |
| F + MSA | 124.9 | 33.2 | — | — |

From the data in Table 1, it will be seen that, in the presence of a catalytic amount of the strong acid, Compounds A, B, D, E and F decomposed at temperatures lower (by about 15°–30° C.) than the same compounds decomposed in the absence of the strong acid.

EXAMPLE 34

Imaging Process of the Invention

This Example illustrates an imaging process of the present invention, in which superacid is generated by ultra-violet irradiation of a film containing a superacid precursor (a sulfonium salt), this superacid is used to catalyze the decomposition of a squaric acid derivative, thereby amplifying the quantity of acid present, and the acid forms a visible image upon lamination of the film to a second film containing an irreversible indicator dye.

Four coating fluids were prepared as follows:

Fluid A

Triphenylsulfonium hexafluoroarsenate (6 mg) and poly(vinyl butyral) (B-76 Butvar, supplied by Monsanto Chemical Corp., 25 mg), dissolved in methyl ethyl ketone (0.5 mL)

Fluid B

As Fluid A, with the addition of 10 mg of Compound A

Fluid C

As Fluid A, with the addition of 15 mg of Compound C

Fluid D

A leuco dye of the formula:

(20 mg; this leuco dye may prepared by the procedure described in U.S. Pat. No. 4,345,017) and poly(vinyl butyral) (B-76 Butvar, supplied by Monsanto Chemical Corp., 25 mg), dissolved in methyl ethyl ketone (0.5 mL).

These four fluids were coated on to a 4 mil (101 μm) poly(ethylene terephthalate) film using a number 8 coating rod to produce coatings A–D respectively.

Coatings A, B and C were then exposed to ultra-violet radiation of 254 nm wavelength from a Spectroline Model ENF-240C ultra-violet lamp (available from Spectronics Corporation, Westbury, N.Y.) for periods of 15, 30, 60 and 120 seconds; one portion of each coating was left unexposed as a control. One portion of each exposed coating was then heated to 90° C. for 20 seconds, while a second portion of each exposed coating was kept at room temperature. Finally, both portions of each exposed coating were separately laminated, with the coated sides in contact, to portions of Coating D, this lamination being effected at a temperature of 180° F. (88° C.) and 60 psi (0.43 MPa). Lamination caused mixing of the coatings, so that any acid present in the exposed portions of Coating A, B or C protonated the indicator dye in Coating D and produced a magenta color, the density of which was proportional to the amount of protonated dye present.

Table 2 below shows the green optical densities produced in each portion of each coating. Coating A, which contains no squaric acid derivative to act as an acid amplifier, is used as a control. For each optical density measured for Coatings B and C, an acid amplification factor ("AAF", i.e., the number of moles of acid liberated from the squaric acid derivative for each mole of superacid which the ultra-violet irradiation liberates from the superacid precursor) was calculated by dividing the difference in optical density between exposed and unexposed portions of the same coating (otherwise treated identically) by the difference between exposed and unexposed portions of Coating A treated in the same manner. The AAF's shown in Table 2 refer to the line coating in the immediately preceding line of the Table.

TABLE 2

| Exposure secs. | 0 | 15 | 30 | 60 | 120 |
|---|---|---|---|---|---|
| Coating | | Green Optical Density | | | |
| A (no heat) | 0.015 | 0.053 | 0.059 | 0.065 | 0.094 |
| A (heated) | 0.018 | 0.035 | 0.036 | 0.050 | 0.062 |
| B (no heat) | 0.061 | 0.214 | 0.425 | 0.705 | 0.860 |
| AAF | — | 4.0 | 8.3 | 12.9 | 10.1 |
| B (heated) | 0.028 | 0.237 | 0.206 | 0.232 | 0.280 |
| AAF | — | 12.3 | 9.9 | 6.4 | 5.7 |
| C (no heat) | 0.027 | 0.199 | 0.346 | 0.909 | 0.887 |
| AAF | — | 4.5 | 7.3 | 17.6 | 10.9 |
| C (heated) | 0.023 | 0.712 | 0.769 | 0.712 | 0.848 |
| AAF | — | 40.5 | 41.4 | 19.7 | 18.8 |

From Table 2, it will be seen that the use of a squaric acid derivative provides very substantial amplification of the acid generated by irradiation of the superacid precursor, with acid amplification factors in excess of 40 being achieved in some instances.

EXAMPLE 35

Imaging Process of the Invention

This Example illustrates an imaging process of the present invention, in which superacid is generated by ultra-violet irradiation of a two-layer film, one layer of which contains a superacid precursor (an iodonium salt), this superacid is used to catalyze the decomposition of a squaric acid derivative, thereby amplifying the quantity of acid present, and the acid forms a visible image upon heating of the film, with consequent mixing of the acid produced with an indicator dye originally present in the second layer of the film.

Four coating fluids were prepared as follows:

Fluid A t-Butyl anthracene (5 mg), (4-n-octyloxyphenyl)phenyliodonium hexafluoroantimonate (10 mg, prepared as per U.S. Pat. No. 4,992,571) and poly(methyl methacrylate) (Elvacite 2021, supplied by DuPont de Nemours, Wilmington, Del.; 30 mg), dissolved in methyl ethyl ketone (0.6 mL)

Fluid B

As Fluid A, with the addition of 20 mg of Compound A

Fluid C

As Fluid A, with the addition of 20 mg of Compound H

Fluid D

As Fluid A, with the addition of 30 mg of the polymer prepared in Example 9 above.

These four fluids were coated on to a 4 mil (101 µm) poly(ethylene terephthalate) film (ICI Type 3295, supplied by ICI Americas, Inc., Wilmington, Del.) using a number 18 coating rod to produce coatings A–D respectively.

To provide the indicator dye layer for the imaging media, an indicator dye coating fluid was prepared as follows. De-ionized water (60 mL) was added dropwise to a magnetically stirred solution of a surfactant (Aerosol TR-70, adjusted with potassium hydroxide to pH 6, 0.65 g), the leuco dye used in Example 13 above (2.5 g), a base (HALS-62, supplied by Fairmount Chemical Company, Inc., 117 Blanchard Street, Newark, N.J. 07105, 0.25 g) and a polymeric binder (Elvacite 2043, supplied by DuPont de Nemours, 2.75 g) in dichloromethane (46 mL). The resultant, very viscous mixture was sonicated, causing the viscosity to decrease, and then allowed to stir overnight at room temperature, during which the dichloromethane evaporated. A fluorinated surfactant (FC-120, supplied by Minnesota Mining and Manufacturing Corporation, St. Paul, Minn., 56 mg of a 25% aqueous solution) was then added. A sample of the resultant dispersion (1 mL) was diluted with an equal volume of a 5% aqueous solution of poly(vinyl alcohol) (Vinol 540). Coatings A–D were then overcoated with the resultant solution using a number 7 coating rod to form imaging Media A–D respectively.

These Media A–D were then imagewise exposed through their film bases to ultra-violet radiation from a Universal UV unit (nominally emitting at 375 nm) supplied by Gelman Instrument Company, then heated on a hot plate at 110° C. for 45 seconds. This heating served to cause decomposition of the squaric acid derivatives in regions in which acid had been generated by ultra-violet irradiation of the sensitized iodonium salt, and to mix the photochemically active layer with the indicator dye layer, thereby producing a visible image whose density was proportional to the amount of protonated indicator dye present (and therefore to the amount of acid generated by the iodonium salt and decomposition of the squaric acid derivatives).

After this heating, the difference in green optical density between exposed and unexposed regions were measured for Media B, C and D using an X-Rite 310 photographic densitometer, supplied by X-Rite, Inc., Grandville, Mich., with the appropriate filter. The ratio of this difference to the difference measured for Medium A, which contained no squaric acid derivative, was the acid amplification factor (AAF) due to the squaric acid derivatives. The results are shown in Table 3 below.

TABLE 3

| Medium | Optical Density Difference | AAF |
|---|---|---|
| A | 0.08 | 1 |
| B | 1.64 | 20.5 |
| C | 0.51 | 6.4 |
| D | 0.62 | 7.8 |

From the data in Table 3, it will be seen that the presence of the squaric acid derivative provided very substantial amplification of the acid produced by ultra-violet irradiation of the superacid precursor.

EXAMPLE 36

Imaging Process of the Invention Using Monomeric Oxalate Derivatives

This Example illustrates an imaging process of the present invention generally similar to that described in Example 35 above, but in which the secondary acid generator is a monomeric oxalate derivative.

A series of coatings were prepared as follows:

t-Butyl anthracene (5 mg), (4-n-octyloxyphenyl)phenyliodonium hexafluoroantimonate (5 mg, prepared as per U.S. Pat. No. 4,992,571) and the secondary acid generator to be tested (15 mg) were dissolved in a 5% solution of poly(vinyl chloride) (OxyChem 160, supplied by Occidental Chemical Co., 5005 LBJ Freeway, Dallas, Tex. 75244) in 2-butanone (MEK). The resultant solution was coated onto poly(ethylene terephthalate) base of 4 mil (101 μm) thickness (P4C1A film, available from E. I. DuPont de Nemours, Wilmington, Del.) using a number 12 coating rod.

Separately, an indicator dye layer was prepared by coating a solution of an indicator dye 3,3-bis-[1-butyl-2-methyl-1H-indol-3-yl]-1-isobenzofuranone (sold commercially under the tradename Copikem 20, by Hilton Davis Co., 2235 Langdon Farm Road, Cincinnati, Ohio 45237, 1.00 g) and a polymer binder Elvacite 2043 (available from E. I. DuPont de Nemours, 1.25 g) in 2-butanone (MEK, 25.0 g) at a coverage of 444 mg/ft$^2$. (Alternatively, an indicator dye layer was prepared by coating an aqueous dispersion substantially as described in Example 35 above, using the following materials and coverages:

- magenta indicator dye, 3,3-bis-[1,2-dimethyl-1H-indol-3-yl]-1-isobenzofuranone (Copikem 3, available from Hilton Davis Co.), 104 mg/ft$^2$;
- hindered amine base, Tinuvin 292 (available from Ciba-Geigy Co., Ardsdale, N.Y.) 26 mg/ft$^2$;
- surfactant Aerosol TR-70 (supplied by American Cyanamid Co., Wayne, N.J. 07470) 13 mg/ft$^2$; and
- polymeric binder Elvacite 2043, 156 mg/ft$^2$.

Experiments using this indicator dye layer are marked by an asterisk in Table 4 below.)

The coatings containing the secondary acid generator were exposed, through a step wedge, to ultraviolet radiation from a 1000W mercury vapor lamp (filtered to remove wavelengths below about 330 nm) in a nuArc 26-1K UV exposure system (available from nuArc company, Inc., 6200 W. Howard St., Niles, Ill. 60648). The irradiance at the film plane was measured using a "Light Bug" radiometer, type IL390B, available from International Light, Inc., Newburyport, Mass. 01950. After exposure, the coating was heated at 65° C. for 20 seconds, then laminated to the indicator dye layer at 250° F. and 60 psig. After lamination, the green density (which is proportional to the total amount of acid generated) achieved was measured in an unexposed region and in eight regions, each of which had received different amounts of ultraviolet exposure.

Table 4 below shows the relationship between UV exposure (in mJ/cm$^2$) and green density attained for the various monomeric oxalate derivative secondary acid generators tested; the column headed "Ex. #" refers to the Example above in which the relevant secondary acid generator was prepared, while "None" in this column refers to a control experiment in which no secondary acid generator was included.

TABLE 4

| Ex. | Green Optical Density After Exposure of (mJ/cm$^2$) | | | | | | |
|---|---|---|---|---|---|---|---|
| | 0 | 3 | 6 | 11 | 26 | 42 | 86 |
| None | 0.04 | 0.05 | 0.08 | 0.10 | 0.18 | 0.26 | 0.42 |
| 12* | 0.06 | 0.07 | 0.07 | 0.23 | 0.51 | 1.03 | 1.51 |
| 13* | 0.38 | 0.99 | 1.41 | 1.17 | 1.28 | 1.49 | 1.49 |
| 14* | 0.38 | 0.99 | 1.41 | 1.17 | 1.28 | 1.49 | 1.49 |
| 15* | 0.08 | 0.10 | 0.14 | 0.32 | 1.00 | 1.00 | 1.11 |
| 16 | 0.08 | 0.09 | 0.12 | 0.26 | 0.81 | 0.88 | 0.99 |
| 18* | 0.06 | 0.09 | 0.16 | 0.76 | 0.75 | 0.83 | |
| 19 | 0.05 | 0.05 | 0.10 | 0.36 | 1.00 | 0.84 | 0.92 |
| 20 | 0.06 | 0.08 | 0.07 | 0.15 | 0.96 | 0.96 | 0.92 |
| 21 | 0.04 | 0.05 | 0.07 | 0.11 | 0.43 | 0.42 | 0.97 |
| 22 | 0.08 | 0.08 | 0.08 | 0.09 | 0.36 | 0.66 | 0.80 |
| 23 | 0.04 | 0.04 | 0.07 | 0.19 | 0.57 | 0.60 | 0.84 |
| 24 | 0.06 | 0.13 | 0.27 | 0.49 | 0.78 | 0.86 | 0.99 |

From the data in Table 4, it will be seen that, at substantial ultraviolet exposures, all of the coatings containing secondary acid generators produced substantially higher green optical densities than the control coating, thus indicating that the oxalate derivative was undergoing superacid-catalysed thermal decomposition and "amplifying" the superacid produced by the ultraviolet exposure.

EXAMPLE 37

Imaging Process of the Invention Using Polymeric Oxalate Derivatives

This Example illustrates an imaging process of the present invention generally similar to that described in Example 36 above, but in which the secondary acid generator is a polymeric oxalate derivative.

A series of coatings were prepared in substantially the same manner as in Example 36 above, except that the polymeric binder was omitted from the test coating. More specifically, t-butyl anthracene (5 mg) and (4-n-octyloxyphenyl)phenyliodonium hexafluoroantimonate (5 mg) and the polymeric oxalate derivative secondary acid generator being tested (45 mg) were dissolved in MEK (0.6 mL), and the resultant solution was coated, exposed, and laminated, and the green optical density measured, all in the same way as in Example 36 above. The results obtained are shown in Table 5 below.

TABLE 5

| Ex. # | Green Optical Density After Exposure of (mJ/cm$^2$) | | | | | | | | |
|---|---|---|---|---|---|---|---|---|---|
| | 0 | 3 | 6 | 11 | 26 | 42 | 86 | 170 | 305 |
| 26 | 0.07 | 0.07 | 0.19 | 0.68 | 0.99 | 0.83 | 0.81 | 0.82 | 1.04 |
| 28* | 0.13 | 0.22 | 0.52 | 0.92 | 0.92 | 1.03 | 1.04 | 1.25 | 1.15 |
| 31 | 0.05 | 0.05 | 0.05 | 0.07 | 0.21 | 0.49 | 0.55 | 1.03 | 0.98 |

From the data in Table 5, it will be seen that, at substantial ultraviolet exposures, all of the coatings containing polymeric secondary acid generators produced substantial green optical densities, thus indicating that the polymeric oxalate derivative was undergoing superacid-catalysed thermal decomposition and "amplifying" the superacid produced by the ultraviolet exposure.

From the foregoing, it will be seen that the present invention provides a process for generation of an acid and for forming an image, and an imaging medium, which permit generation of a strong acid in substantially greater quantity (and thus with greater sensitivity) than by simple irradiation of a superacid precursor.

We claim:

1. An imaging medium comprising:

a superacid precursor capable of generating a superacid upon exposure to actinic radiation;

a secondary acid generator capable of undergoing thermal decomposition to produce a secondary acid, the thermal decomposition of the secondary acid generator being catalyzed by the superacid; and an acid-sensitive material which changes color in the presence of the secondary acid liberated when the secondary acid generator is decomposed.

2. An imaging medium according to claim 1 wherein the superacid precursor comprises a diphenyliodonium compound.

3. An imaging medium according to claim 2 wherein the superacid precursor comprises a triphenylsulfonium or diphenyliodonium compound.

4. An imaging medium according to claim 1 further comprising an acid sensitive material which changes color in the presence of the secondary acid liberated when the secondary acid generator is decomposed.

5. An imaging medium according to claim 4 wherein the acid sensitive material is admixed with an amount of a basic material sufficient to neutralize all the acid which could be liberated by the superacid precursor.

6. An imaging medium according to claim 4 comprising a first layer or phase containing the superacid precursor and the secondary acid generator and a second layer or phase containing the acid sensitive material.

7. An imaging medium according to claim 1 wherein the superacid precursor and the secondary acid generator are under essentially anhydrous conditions.

8. An imaging medium according to claim 1 further comprising a polymeric binder in which the superacid precursor and the secondary acid generator are dispersed.

* * * * *